(12) United States Patent
Patzke

(10) Patent No.: US 6,317,702 B1
(45) Date of Patent: Nov. 13, 2001

(54) METHOD FOR INSTRUMENT DETERMINATION OF A MEASURED VARIABLE WHICH CHANGES WITH TIME

(75) Inventor: Jürgen Patzke, Marburg (DE)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 09/503,152

(22) Filed: Feb. 11, 2000

Related U.S. Application Data

(63) Continuation of application No. 08/936,544, filed on Sep. 24, 1997, now Pat. No. 6,044,330.

(30) Foreign Application Priority Data

Sep. 28, 1996 (DE) .............................................. 196 40 121

(51) Int. Cl.⁷ ........................... G01N 31/00; G01N 33/00
(52) U.S. Cl. ........................ 702/189; 436/517; 356/341
(58) Field of Search ........................ 702/189, 19, 29; 436/517, 819, 543, 805; 356/341, 338, 339; 70/32; 435/7.1, 7.91, 68.1; 352/442

(56) References Cited

U.S. PATENT DOCUMENTS

| | | | |
|---|---|---|---|
| 3,990,851 | 11/1976 | Gross et al. | 436/815 |
| 4,157,871 | 6/1979 | Anderson et al. | 356/341 |

(List continued on next page.)

FOREIGN PATENT DOCUMENTS

| | | |
|---|---|---|
| 33 47 162 | 7/1985 | (DE) . |
| 0 252 127 | 7/1988 | (EP) . |

OTHER PUBLICATIONS

Wentzell, et al., "Reaction–Rate Method of Analysis Insensitive to Between–Run Changes in Rate Constant," *Anal. Chem. 58*, pp. 2851–2855, 1986.

Love, et al., "Systematic comparison of data–processing options for kinetic–based single–component determinations of non–catalysts Part 1. Review, systematic classification, mathematical descriptions, performance characteristics and perspectives," *Analytica Chimica Acta 299*, pp. 195–208, 1994.

Love, et al., "Systematic comparison of data–processing options for kinetic–based, single–component determinations of noncatalysts: Effects of random noise," *Analytica Chimica Acta 326*, pp. 95–106, 1996.

(List continued on next page.)

*Primary Examiner*—Kamini Shah
*Assistant Examiner*—Edward Raymond
(74) *Attorney, Agent, or Firm*—Finnegan, Henderson, Farabow, Garrett and Dunner, L.L.P.

(57) ABSTRACT

The present invention relates to a method for instrument determination of measured variable L(t) which changes with time, the intention being to determine the maximum rate value of L(t) in a region with a linear reaction profile, and the time as well as the duration of the reaction time window being variable with the linear region and depending on the nature of the reaction and the reaction conditions. Specifically, the present invention relates to the determination of protein concentrations with the aid of light scatter, which is produced by specific antibodies, in homogeneous solutions. In particular, the invention relates to reactions which take place slowly and have a largely linear profile over a relatively long time, the rate of formation of antigen-antibody complexes in the linear section of the reaction ($V_{MaxLin}$) being determined as the measured variable.

38 Claims, 18 Drawing Sheets

TABLE 1 DIAGRAM 3

U.S. PATENT DOCUMENTS

| | | | |
|---|---|---|---|
| 4,581,337 | 4/1986 | Frey et al. | 436/534 |
| 5,244,815 | 9/1993 | Guirguis | 501/139 |
| 5,635,602 | 6/1997 | Cantor et al. | 530/391.1 |
| 5,705,353 | 1/1998 | Oh et al. | 435/7.92 |

OTHER PUBLICATIONS

Whicher, et al., "Immunoephelometric and Immunoturbidimetric Assays for Proteins," *CRC Critical Reviews in Clincial Laboratory Sciences*, vol. 18, Issue 3, pp. 213–260, 1983.

Price, et al., "Light–scattering immunoassay of specific proteins: a review," *Ann Clin Biochem 20*, pp. 1–14, 1983.

Holler, et al., "Minimization of Errors in Fixed–Time Reaction Rate Methods by Optimization of Measurement Time," *Analytical Chemistry*, vol. 54, No. 4, pp. 755–761, Apr., 1992.

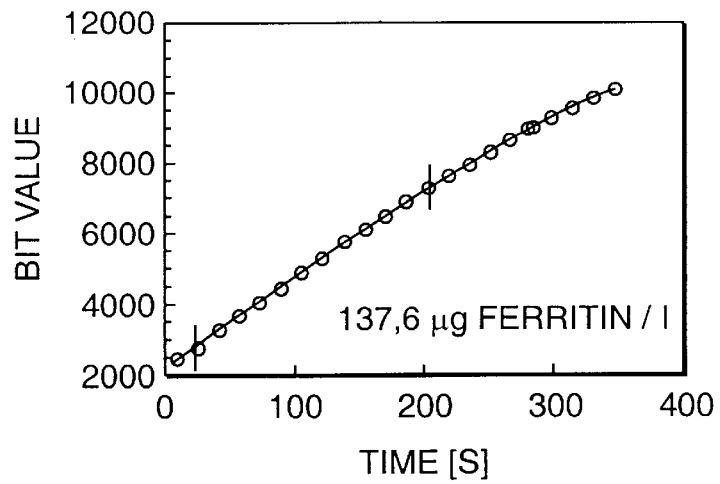
FIG. 1a (1)
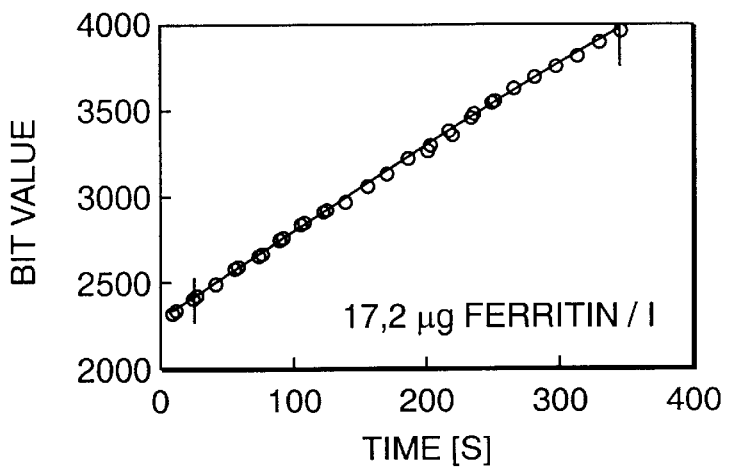
FIG. 1a (2)
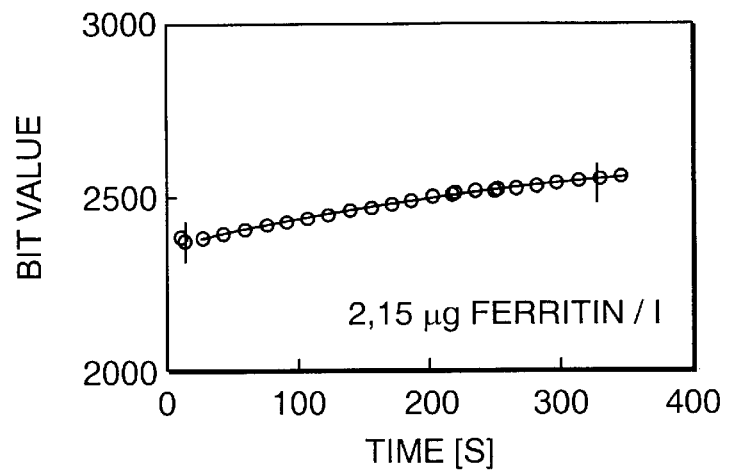
FIG. 1a (3)

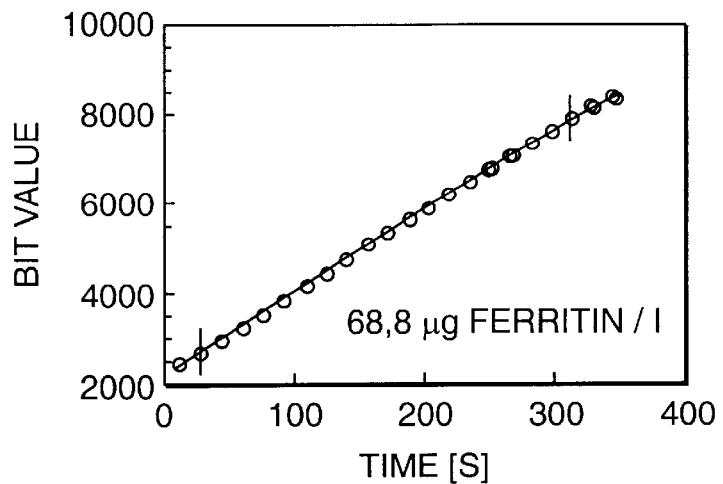
FIG. 1b (1)
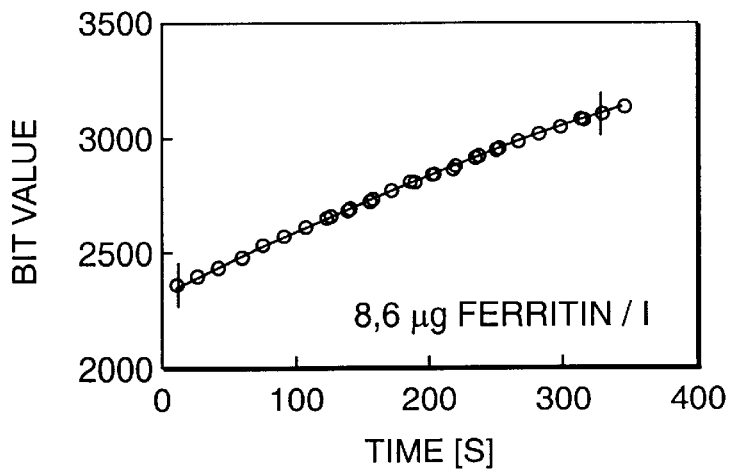
FIG. 1b (2)
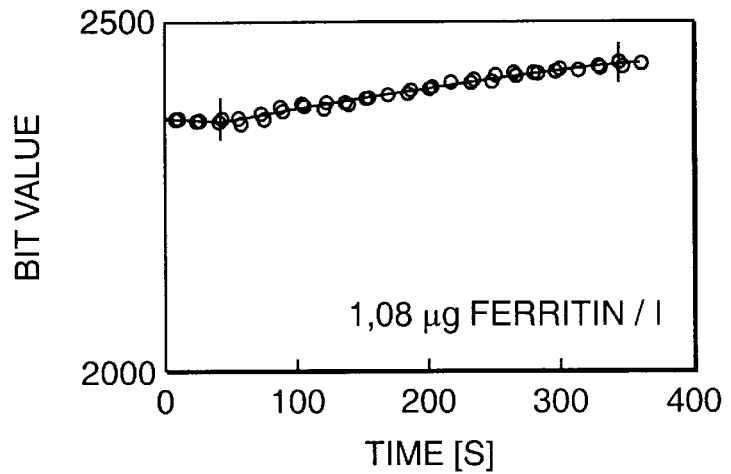
FIG. 1b (3)

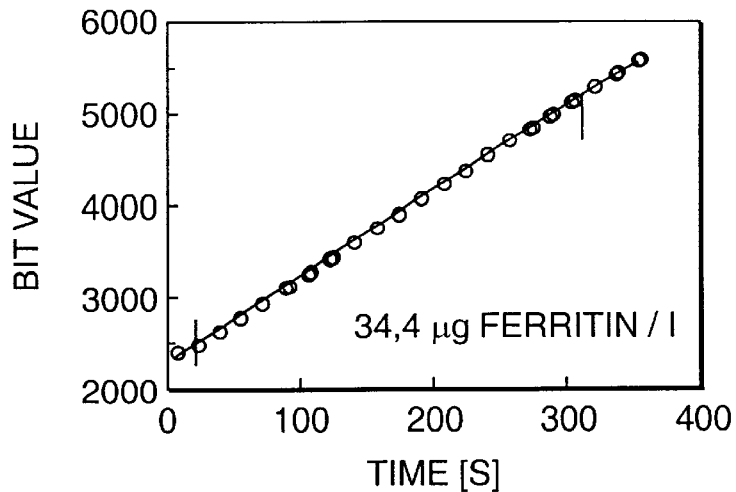
FIG. 1c (1)
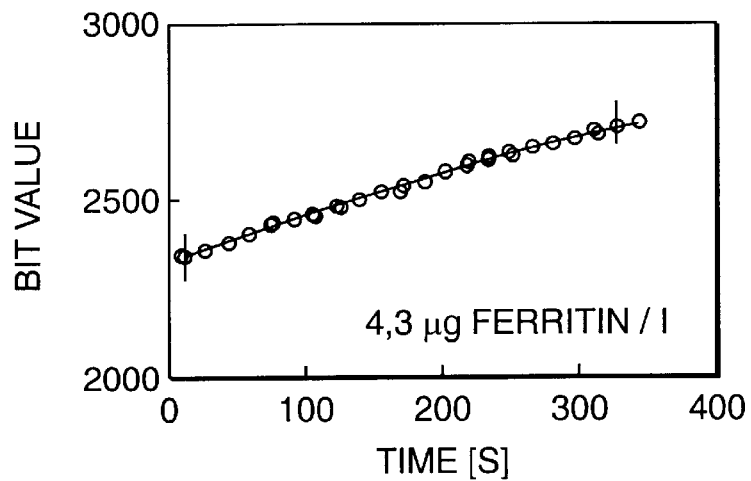
FIG. 1c (2)
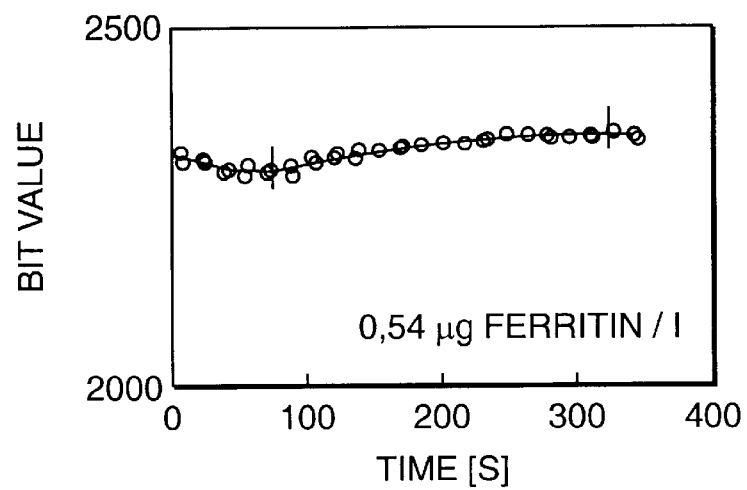
FIG. 1c (3)

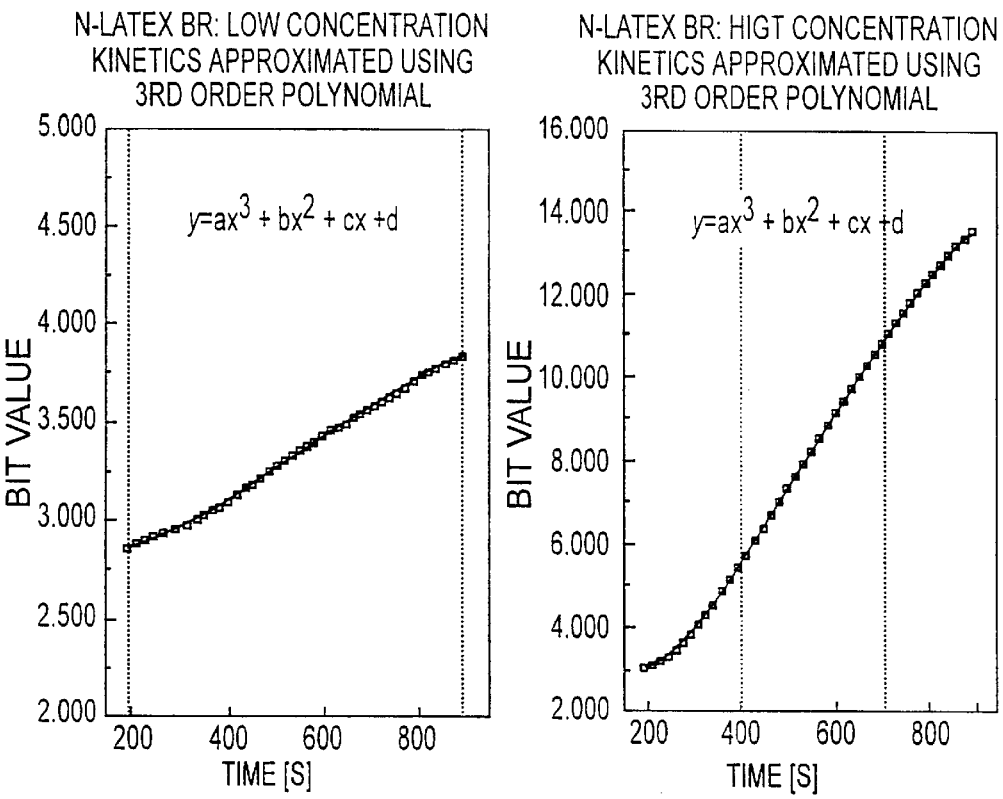
FIG. 5a
FIG. 5c
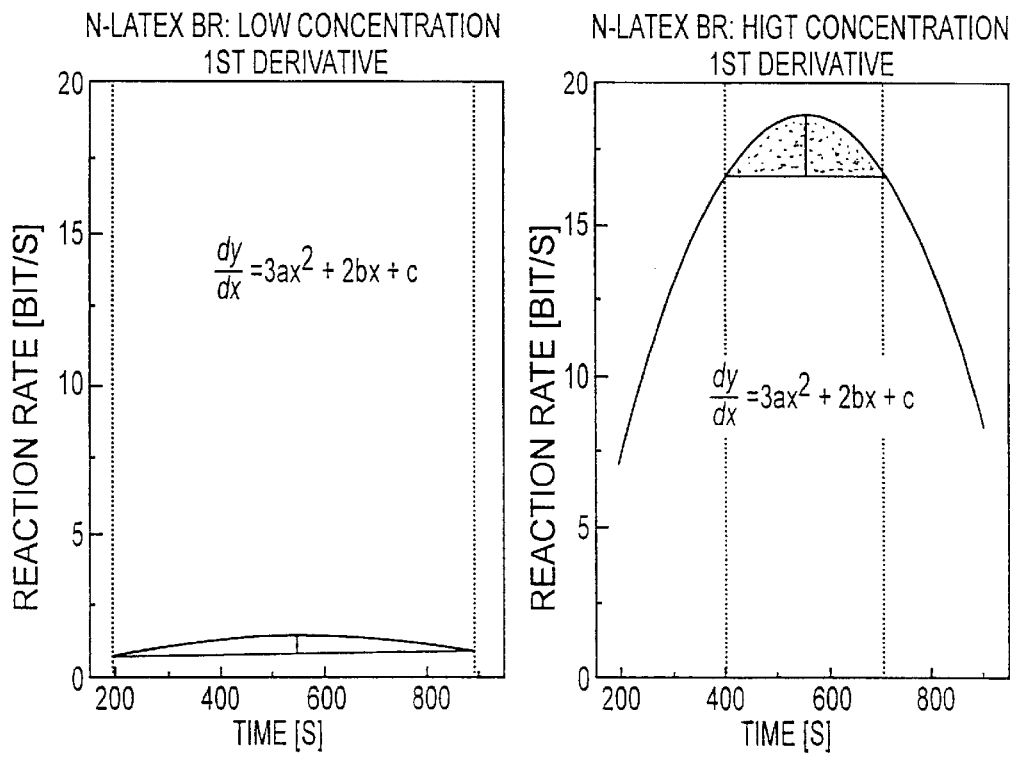
FIG. 5b
FIG. 5d

TABLE 1

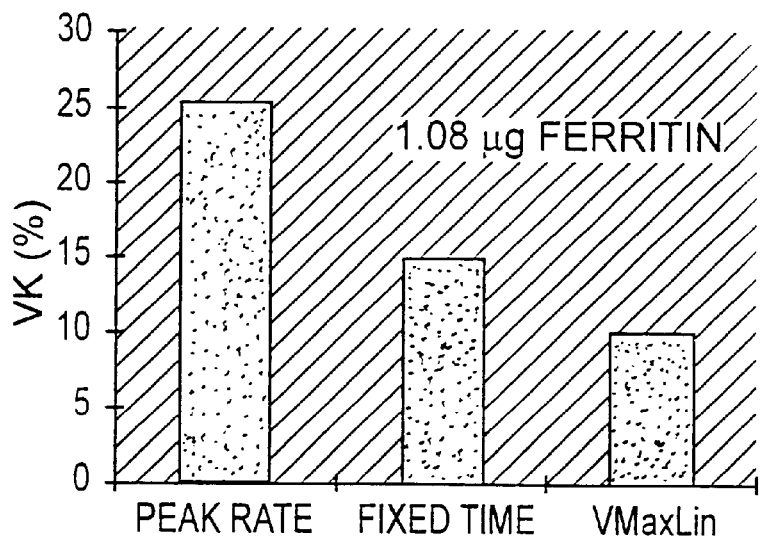

INTRA ASSAY VARIATION COEFFICIENT AT LOW ANALYT CONCENTRATION

DETERMINATION OF THE VARIATION COEFFICIENT FROM 10 MEASUREMENTS IN THE SERIES OF DILATION OF THE N-FERRITIN STANDARD, HUMAN AND DETERMINATION OF THE MEASURED VALUE BY VARIOUS METHODS. FOR THE PEAK-RATE METHOD, THE MAXIMUM REACTION RATE WAS DETERMINED USING A FIXED REACTION WINDOW WITH A DURATION OF 80 SECONDS. (10 MEASUREMENT POINTS).
FIG. 1 SHOWS AN EXAMPLE OF A REACTION PROFILE FOR A LOW-CONCENTRATION SAMPLE.

*FIG. 7*

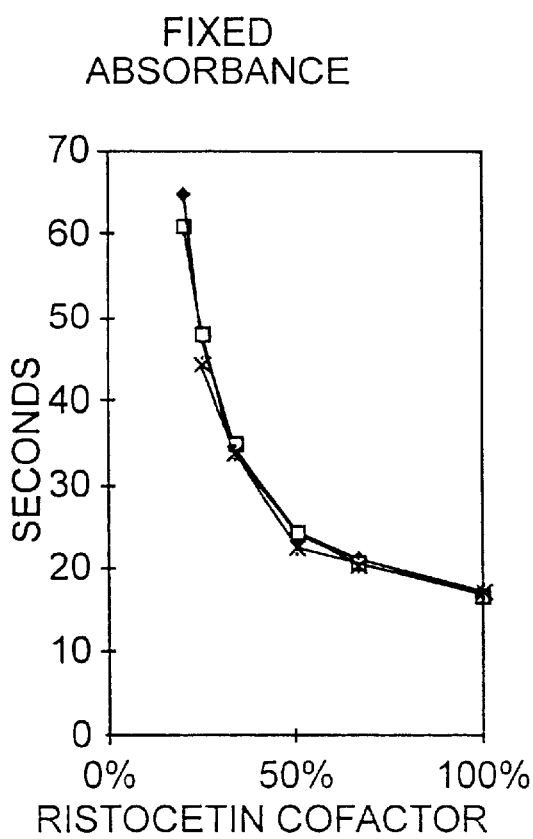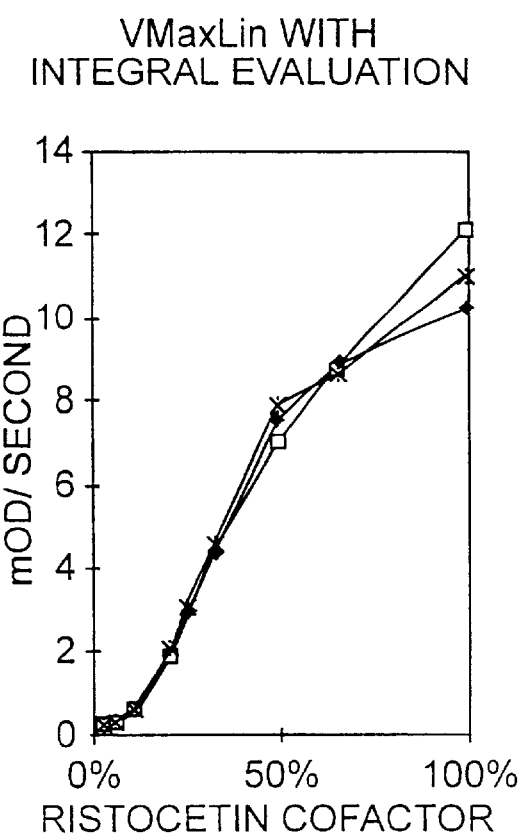
FIG. 13a  FIG. 13b

METHOD FOR INSTRUMENT DETERMINATION OF A MEASURED VARIABLE WHICH CHANGES WITH TIME

This is a continuation of application Ser. No. 08/936,544, filed Sep. 24, 1997 now U.S. Pat. No. 6,044,330.

BACKGROUND OF THE INVENTION

The present invention relates to a method for instrument determination of a measured variable L(t) which changes with time, the intention being to determine the maximum value of L(t) in a region with a linear reaction profile, and the time as well as the size of the reaction time window being variable with the linear region and depending on the nature of the reaction and the reaction conditions. Specifically, the present invention relates to the determination of protein concentrations with the aid of light scatter, which is produced by specific antibodies, in homogeneous solutions. In particular, the invention relates to reactions which take place slowly and have a largely linear profile over a relatively long time, the rate of formation of antigen-antibody complexes in the linear section of the reaction being determined as the measured variable.

The phenomenon of light scatter on particles in a homogeneous medium is used for concentration determination, both by measuring the scattered light intensity (nephelometry) and by measuring the intensity loss of the light beam passing through the medium (turbidimetry).

The immunochemical reaction between a soluble antigen and a bivalent or polyvalent antibody leads to large groups of molecules which scatter light to a major extent. The time profile of such reactions very frequently corresponds to the general kinetic profile of successive first order reactions and has a point of inflection, so that the maximum rate of reaction does not occur until during the course of the reaction (see, for example, FIGS. 1a–1c). A concentration-dependent measurement signal can be obtained in various ways from the signal-time curves in FIGS. 1a–1c.

The intensity of the signal change can be increased by bonding one of the reaction partners to particles, for example in the "particle-enhanced assays" known per se to a person skilled in the art.

In the end-point method, the measurement signal is determined at a time which is so late that, on the basis of experience, it is no longer changing but no precipitation is taking place. In the "fixed time" method, the actual measurement method is the difference between two signals which are determined at times that are different but are fixed in advance.

In the kinetic "peak rate method", the maximum rate of reaction ($V_{Max}$), that is to say the maximum change ($\delta$) of the signal (S) per unit time ($\delta t$), is determined a) by measurements of $\delta S$ at sufficiently short time intervals ($\delta t$) and determination of the maximum quotient $\delta S/\delta t$, b) electronic differentiation $\delta S/\delta t$ and determination of the maximum, c) construction of the tangent to the signal/time curve and determination of the maximum gradient S=signal, t=time.

The method according to the invention can in principle be used for all determinations of a measured variable which varies with time, provided the change in the measured variable is linear only in a sub-region and is intended to be used for evaluation of the linear part.

A large number of analytes can now be quantified by direct or indirect scattered light measurement using the described methods. If one considers the dependency of a suitable measurement signal on the concentration of a reaction partner, for example the antigen, while the other reaction partner is used with a constant concentration, then, for example, it is possible in the case of immunochemical reactions to observe that the same measurement signal can be caused by both a low concentration and a high concentration of the analyte. This leads to an ambiguity in the signal concentration relationship, which is known to the person skilled in the art as the antigen excess phenomenon "high-dose hook" or Heidelberger curve. This ambiguity can in principle be observed wherever complexes of different stoichiometry are possible, depending on the excess amount of one reaction partner or the other, and the signal characteristic, for example scattered light, of these complexes does not differ.

Such immunochemical determination methods are known per se to the person skilled in the art, for example from EP 0 252 127.

In addition to the possible ambiguity in the signal concentration relationship, a further problem is the determination of low concentrations and the evaluation of reactions which take place slowly. The reaction profile of the antigen-antibody bonding in principle has a lag-phase at the start, a region where the rate of reaction is a maximum and a saturation region (FIGS. 1a–1c). The extent to which these three phases are pronounced is very heavily dependent on the concentration of the antigen of the antibody and, furthermore, on a large number of other factors, such as the temperature and the dilution medium, although these are kept as constant as possible in a test system.

The present invention was thus based on the technical problem of providing an immunochemical determination method with the aid of light scatter produced by specific antibodies, which method not only allows very low concentrations to be measured but also offers a high level of protection against the "high-dose hook" effect.

This technical problem is solved by the provision of the embodiments described in the claims.

The essential part of the method according to the invention is that the measurement time window of the respective reaction is adapted by suitable technical steps such that the evaluation takes place reliably in the linear region and the region of the maximum rate of reaction of the time-dependent reaction. The result of such evaluation is $V_{MaxLin}$ which sometimes is also called $X_{lin}$.

The method according to the invention can be ensured by various technical embodiments.

Analytes for the purposes of the invention are plasma proteins such as Ferritin, PSA, IgA, IgG and proteins which can be ascribed to the field of coagulation, such as D-Dimer and clotting factors, in particular genetic variants of clotting factors and, furthermore, haptenes such as hormone and messenger peptide.

The method according to the invention can also advantageously be used for determining the functionality of the clotting system, such as quick test and aPTT; that is, an activated partial thromboplastin time.

It has thus surprisingly been found that the determination method described in the following text not only allows the measurement of low concentrations but also ensures increased protection against the "high-dose hook" effect.

BRIEF DESCRIPTION OF THE DRAWINGS

FIGS. 1a(1) to 1c(3) show concentration dependent measurement signals of Ferritin v. time. The various concentration of ferritin (in μ/l) are as follows: FIG. 1a(1)-137.6; FIG. 1a(2)-17.2; FIG. 1a(3)-2.15; FIG. 1b(1)-68.8; FIG. 1b(2)-8.6; FIG. 1b(3)-1.08; FIG. 1c(1)-34.4; FIG. 1c(2)-4.3; and FIG. 1c(3)-0.54.

FIGS. 3a and 3c show low-concentration sample runs. FIGS. 3b and 3d show normal-concentration sample runs.

FIGS. 5a to 5d show kinetics approximated using third order polynomial and its first derivative. FIGS. 5a and 5b show one low-concentration run and its first derivative. FIGS. 5c and 5d show one high-concentration sample run and its first derivative.

FIG. 7 shows intra assay variation coefficient at low analate concentration.

FIGS. 13a and 13b show results of a Von Willebrand-Assay.

Figure 2:
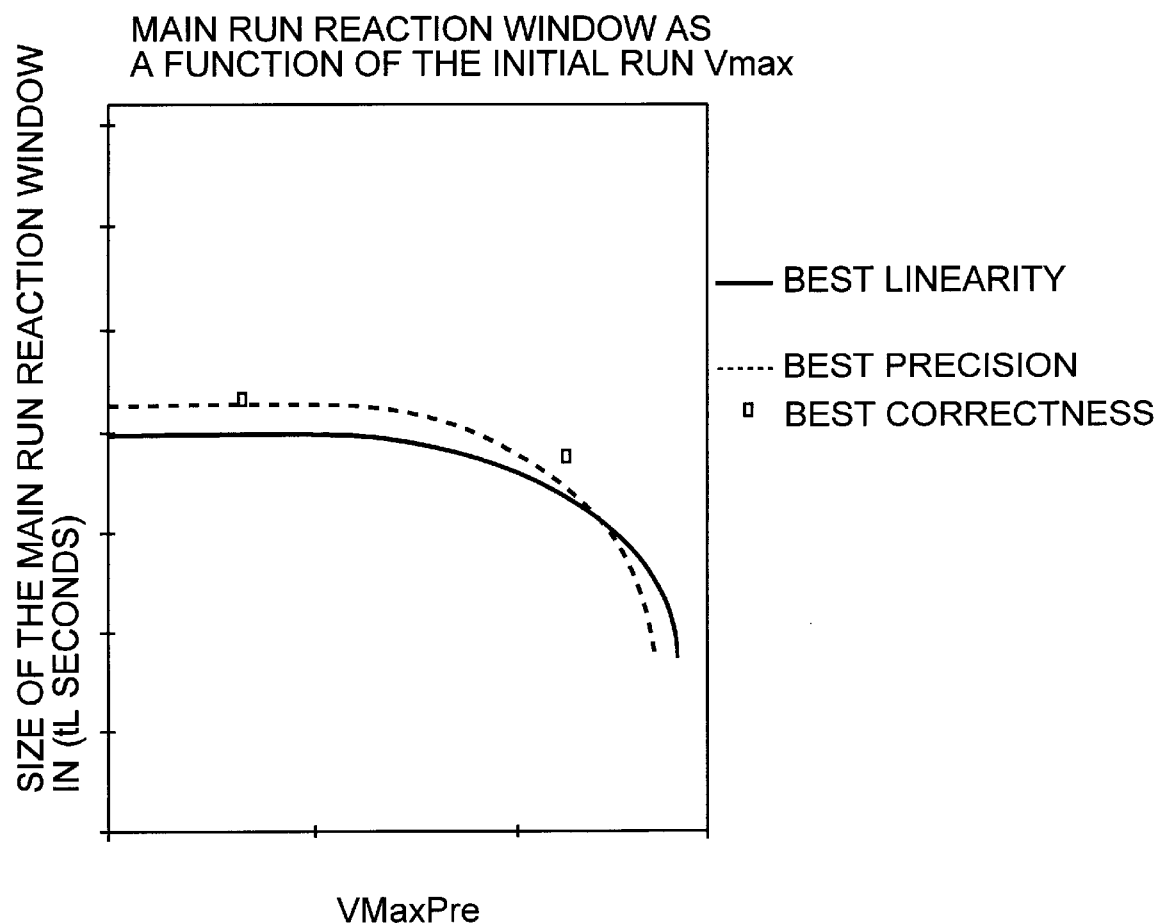
FIG. 2 shows the main run reaction window as a function of the initial run $V_{Max}$.
Figure 3A:
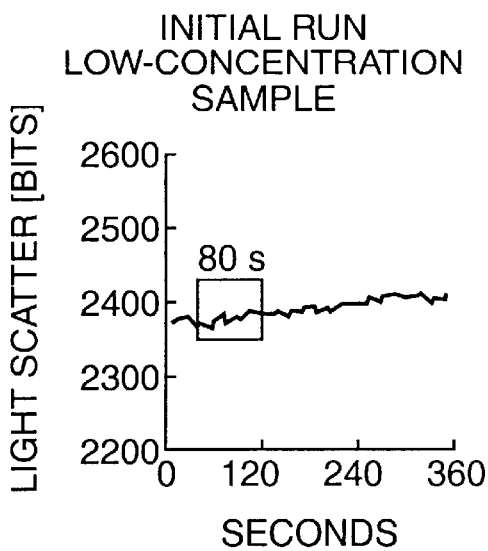
FIGS. 3a to 3d show the $V_{MaxLin}$ method with a two-stage evaluation using several samples.
Figure 3B:
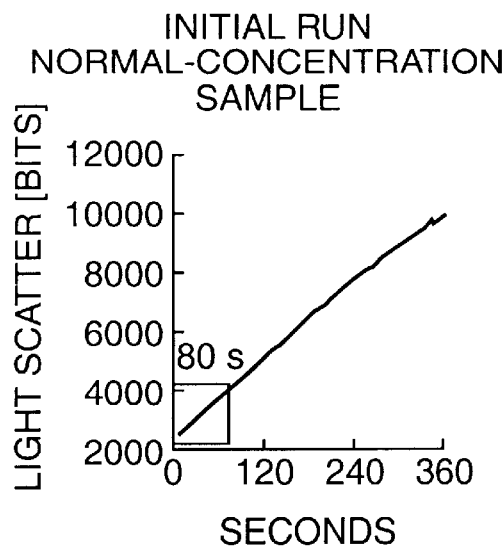
Figure 3C:
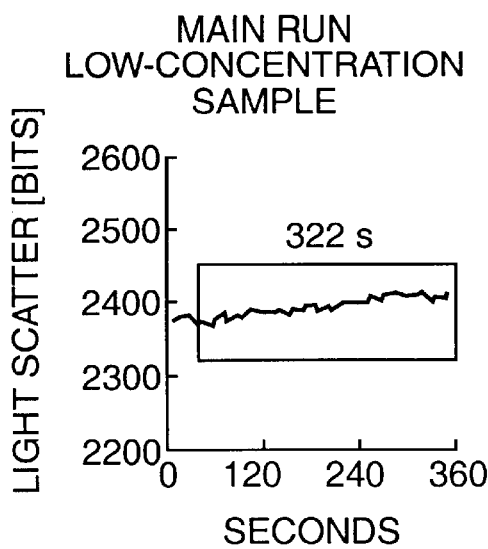
Figure 3D:
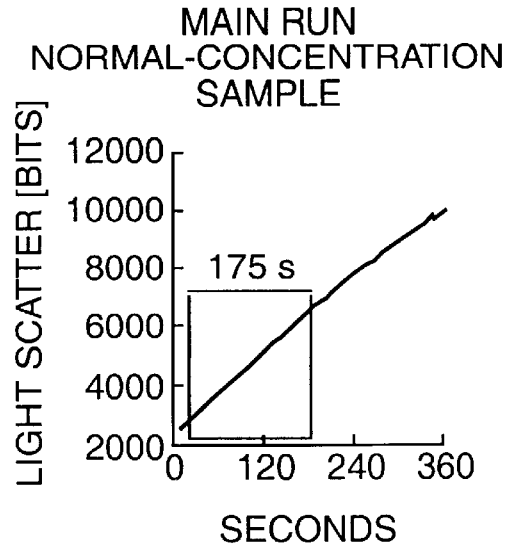

The method according to the invention is carried out in two stages, a sample being measured and the stored reaction kinetic being used for each stage. In the first stage, a relatively short time window is used to determine the initial maximum rate of reaction. The length of the time window $t_{Test}$ is preferably set such that, on average and over a plurality of measurements and batches, it corresponds to the length, of the linear reaction section for the reaction kinetics of samples whose concentration is at the upper end of the measurement range. It also becomes clear from this that the size of the initial reaction window is a test-specific parameter which is dependent, inter alia, on the analyte as well as the test system or verification system used. The $V_{MaxPre}$ determined in this way is used to determine the optimum reaction time window. The dependency between $V_{MaxPre}$ and the optimum reaction time window $t_{Lin}$ must be determined in a test-specific manner in preliminary experiments (FIG. 2). The important factor in this case is that a reaction window is determined for each $V_{MaxPre}$, that on the one hand includes as many measurement points as possible, but on the other hand also considers only points which are on the linear section of the reaction.

Various methods can be used to determine the test-specific dependency. The important factor in this case is that the dependency between $V_{MaxPre}$ and the reaction time window size is defined such that the precision and correctness are optimized. This dependency can be de-fined, for example, by measurements on a pool of serum samples of different analyte concentration or serum standards with different dilution. The concentrations in this case advantageously extend over the entire desired measurement range. In a first step, all the samples are measured, the kinetics are stored and the values of $V_{MaxPre}$ are determined. Different correlation coefficients are now obtained for each sample measurement by changing the reaction window step by step. The window size having the best correlation coefficient is that which also takes best account of the linear section of the reaction. Another suitable measure of linearity is the average distance between the measurement points and the linear regression line. Thus, first of all, the best $t_{Lin}$ for linearity is obtained for each sample with a specific $V_{MaxPre}$. The result for all samples with different $V_{MaxPre}$ is a relationship between $V_{MaxPre}$ and the main run reaction window size $t_{Lin}$ for the best linearity in the reaction window. By way of example, FIG. 2 shows the relationship between the main run reaction window size $t_{Lin}$ and $V_{MaxPre}$ for the best correlation co-efficient.

This relationship is used to produce a reaction curve with standard serum dilution steps of known concentration ($V_{MaxPre}$→main run reaction window size→main run $V_{Max}$)

Since there is no certainty that the criterion of linearity will also provide the best results for precision measurements and for control recovery, the relationship between the main run reaction window and $V_{MaxPre}$ is now finely adjusted. The reference curve produced above is not changed in this case, in order to avoid varying too many parameters at the same time.

Inter-assay and intra-assay precision measurements (intra-assay=in series, inter-assay=on different days) are carried out for various concentration levels of samples, standards and controls, the main run $V_{Max}$ determinations being carried out with reaction windows of different size. The outcome of this is that a main run reaction window size which gives the best precision is obtained for each measurement and thus for each $V_{MaxPre}$. Combination of all the measurements results in a similar dependency as that in the case of linearity. FIG. 2 shows an example of a profile.

The procedure, which is in principle the same, for measuring the control material gives the best correctness (FIG. 2).

It is now possible to select an assignment of main run reaction window size $t_{Lin}$ to $V_{MaxPre}$ which ensures not only good precision but also good recovery of control nominal values. Table 1 shows the result for Ferritin.

Once this relationship between $t_{Lin}$ and $V_{MaxPre}$ has been defined, the calculation of the reference curve must be repeated with the new criteria. The new method can now be characterized completely, as is shown in summary form in Table 1 using the example of Ferritin.

Table 1

The $V_{MaxPre}$ method using the example of Ferritin $V_{MaxLin}$ Parameters for Ferritin Minimum reaction window: 40 seconds
Initial run reaction window: 80 seconds

| $V_{MaxPre}$ | | $t_{Lin}$ |
| --- | --- | --- |
| >25 bit/s | → | 80 seconds |
| 20–25 bit/s | → | 240–160 seconds |
| 10–20 bit/s | → | 360–240 seconds |
| <10 bit/s | → | 360 seconds | a) Low-concentration Sample with Minimum (FIG. 3)

Minimum found at: 38 seconds
$V_{MaxPre}$: 0.270 bit/s (38–118 seconds)
$t_{Lin}$: 360 seconds $V_{MaxLin}$: 0.123 bit/s (38–360 seconds)

b) Normal-concentration Samples without a Minimum (FIG. 3)

Minimum found at: 0 seconds

| $V_{MaxPre}$: 24.02 bit/s | (0–80 seconds) |
|---|---|
| $t_{Lin}$: 175 seconds | |
| $V_{MaxLin}$: 23.64 bit/s | (23–198 seconds) |

It must be stressed that the parameters determined in this way are highly specific for the test system. A test system includes the analyzer, the measurement instructions and the reagents for determining a specific analyte, if necessary with batch-specific differences, and, of course, the sample material.

It is also possible to assess the linearity of the measurement curve for each measurement using mathematical linearity criteria and to evaluate only that part of the curve which corresponds to these predetermined criteria. However, this gives poor precision even with low analyte concentrations.

A further option for determining $V_{Max}$ would be to match a polynomial to the measurement curve of a given sample and then to form the first derivative of the polynomial. The maximum of the first derivative indicates the maximum rate of reaction, although it has been found that, particularly in reactions with a high level of scatter, a $V_{Max}$ determined in this way cannot be relied on, as can be seen, for example, from Table 2 (polynomial).

TABLE 2

Determination of $V_{Max}$ directly from the 3rd order polynomial

| Dilution 1: | Concentration [µg/l] | Polynomial | | Integral | |
|---|---|---|---|---|---|
| | | MW [bit/s] | VK [%] | MW [bit/s] | VK [%] |
| 2.5 | 137.60 | 25.50 | 2.0 | 25.24 | 2.0 |
| 5 | 68.80 | 18.09 | 3.4 | 17.65 | 3.4 |
| 10 | 34.40 | 9.61 | 4.8 | 9.44 | 4.9 |
| 20 | 17.20 | 4.91 | 3.3 | 4.61 | 3.0 |
| 40 | 8.60 | 2.45 | 7.8 | 2.11 | 2.2 |
| 80 | 4.30 | 1.19 | 7.6 | 0.98 | 4.8 |
| 160 | 2.15 | 0.58 | 16.3 | 0.46 | 3.5 |
| 320 | 1.08 | 0.34 | 38.6 | 0.22 | 9.7 |
| 640 | 0.54 | 0.17 | 48.6 | 0.09 | 15.0 |

Surprisingly, it is has been possible to show that, by adaptation of a test-specific integral area below the first derivative of the polynomial, a measurement time period $t_{Lin}$ can be determined in which the measurement curve can be evaluated using linear regression and leads to a result which, with regard to linearity, precision and correctness, is equivalent to the method described above. The size of the integral area is test-specific, i.e. it is preferably determined empirically for each test method and each analyte, and possibly for specific test equipment as well.

Figure 4A:
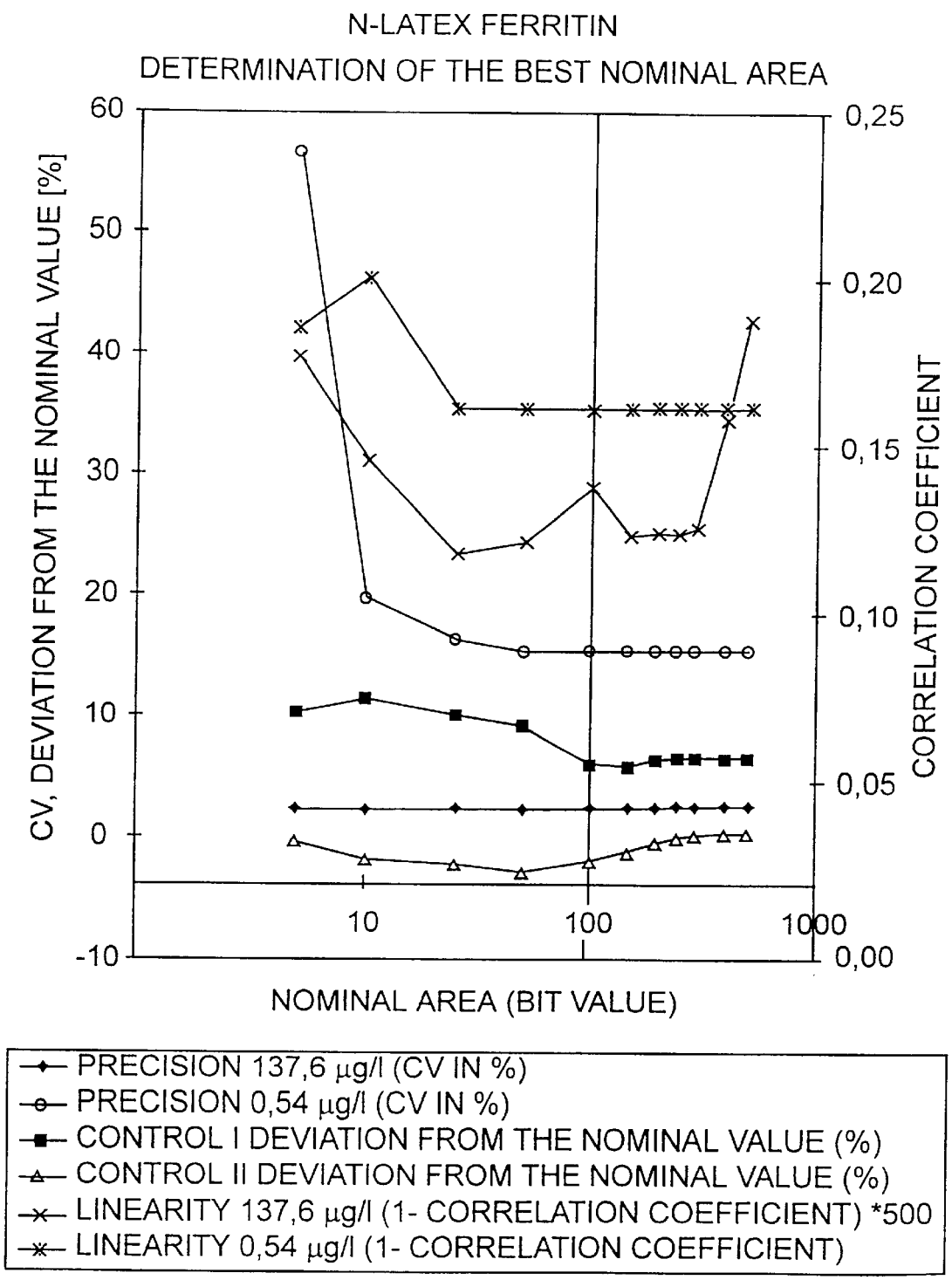
FIG. 4 shows a determination of the precision (CV, %), the deviation from the nominal value (% deviation), and the linearity (correlation coefficient) versus nominal area.
Figure 4B:
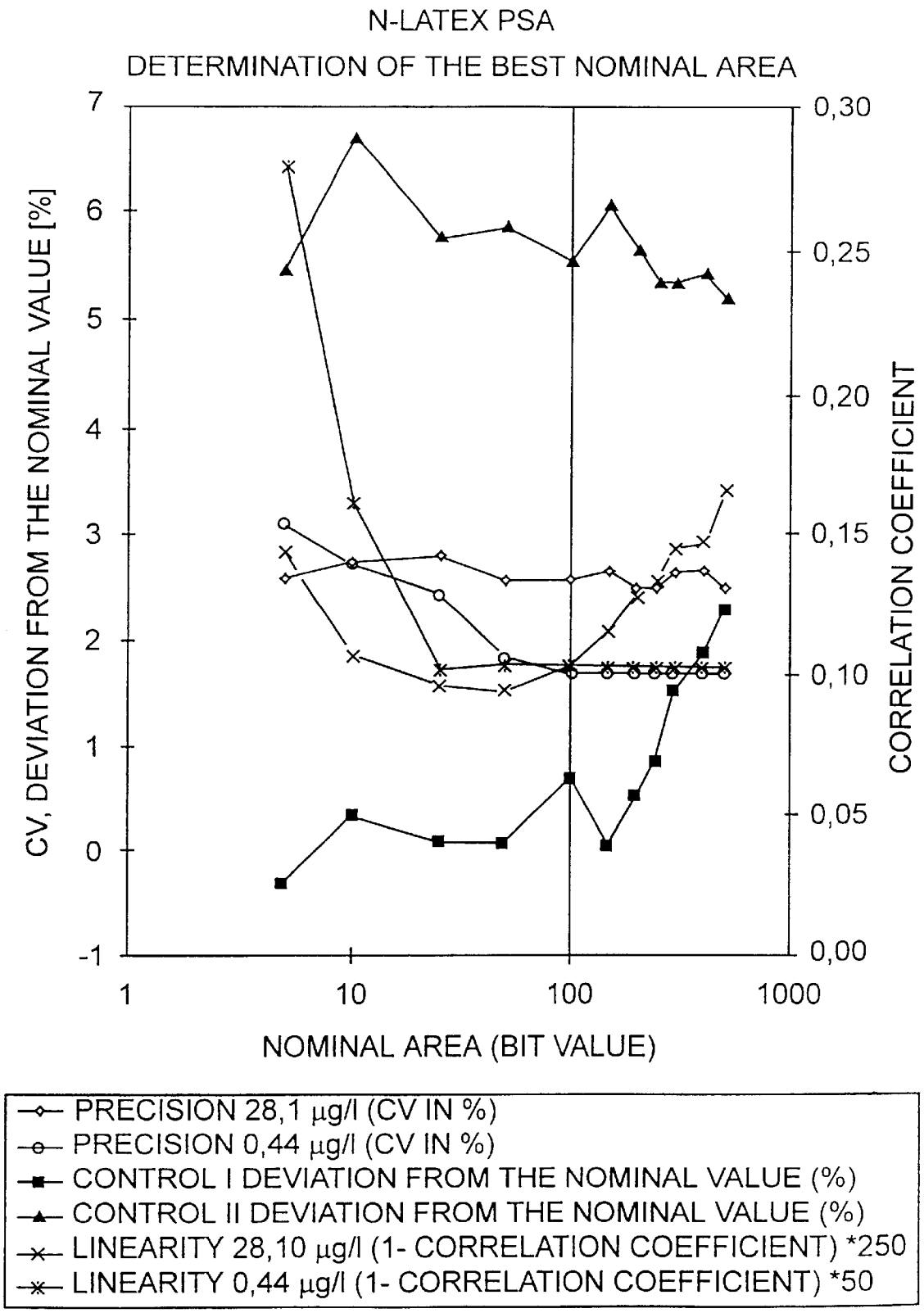
Figure 4C:
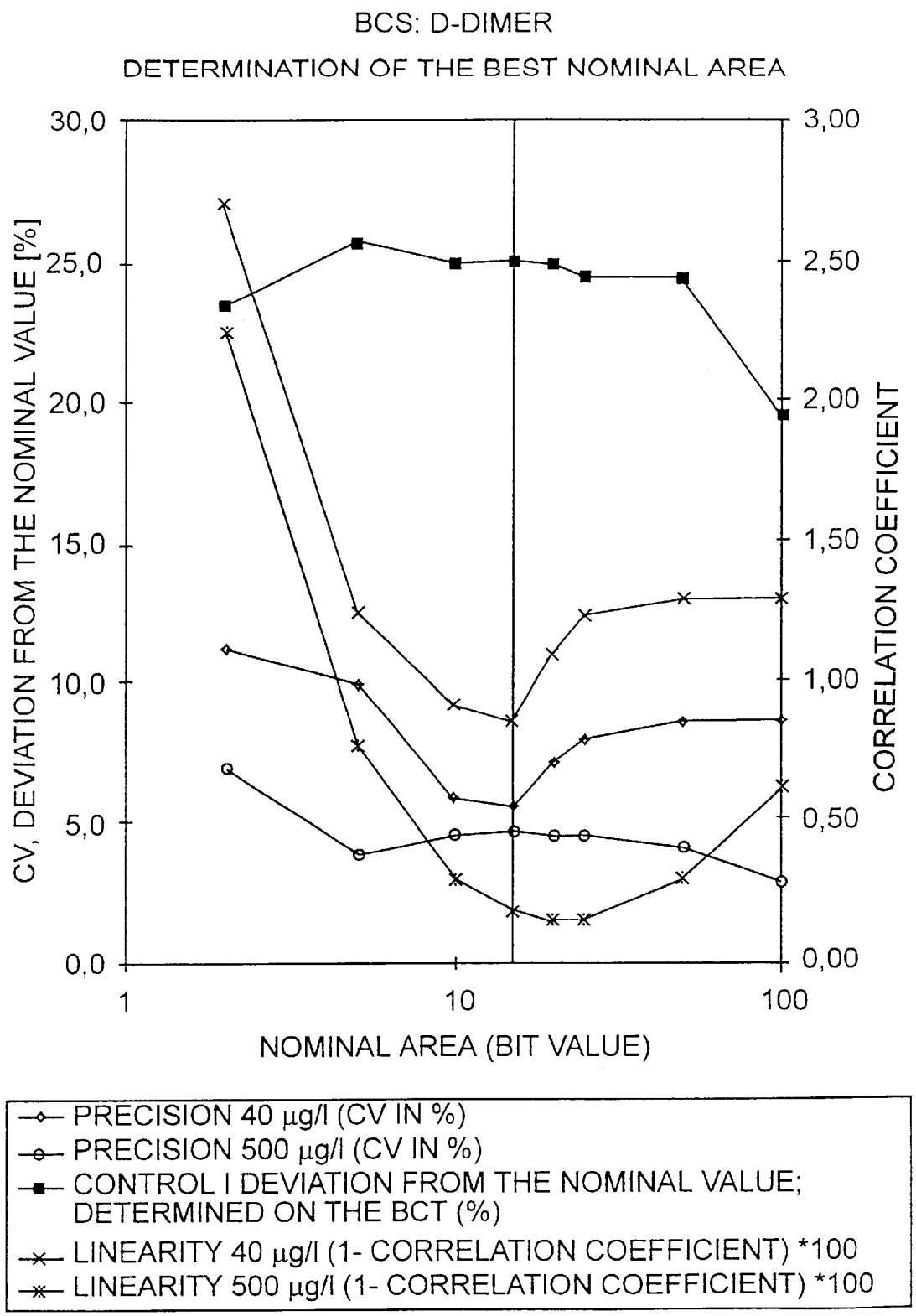
Figure 4D:
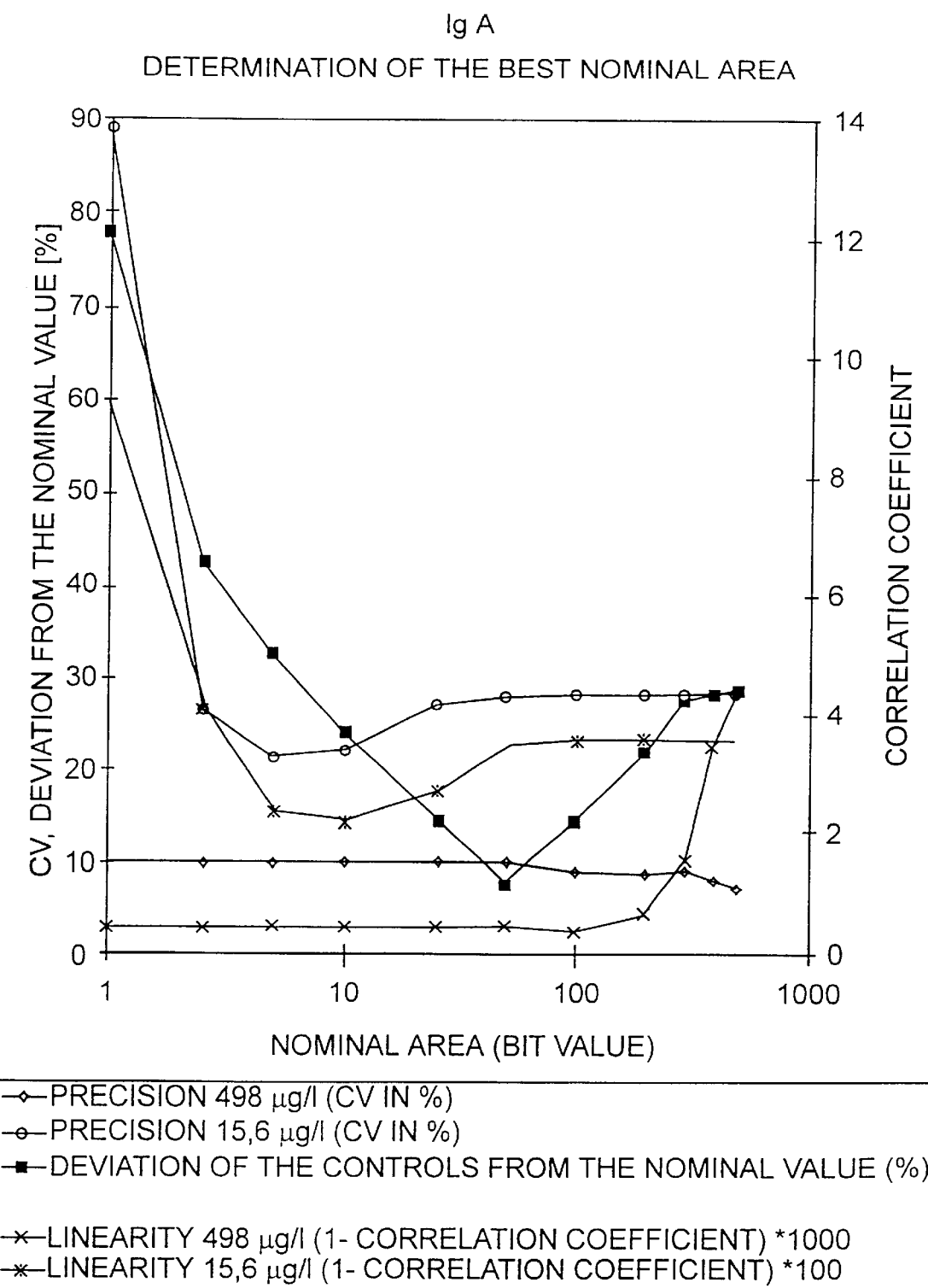

For instance, it has been found to be possible to obtain optimum results with an integral area of 100 for various latex-enhanced tests on a specific equipment (BN II, Behringwerke AG, Marburg), for example for Ferritin and prostate-specific antigen (FIGS. 4a and b). With the same equipment, the best integral area obtained for tests that are not latex-enhanced (FIGS. 4d and e) is 10. With a different equipment (BCS, Behringwerke AG, Marburg), the best area obtained for the latex-enhanced test with a photometric measurement is 20 (FIG. 4c).

The empirical determination of the optimum integral area is carried out in a seperate run as the determination of the dependency between $V_{MaxPre}$ and $t_{Lin}$, but the integral area determined for this variant is a constant which applies to all concentrations. The examples in FIG. 4 each show a very high and a very low concentration. Thus, for example, precision measurements were carried out in series for each reference point to determine the precision of the various latex-enhanced tests using the Behring nephelometer (Behringwerke AG, Marburg). Linearity was obtained for each measurement by the correlation coefficient of the linear regression. Correctness was determined by measuring control serums and convolution on a reference curve, likewise evaluated using the integral method.

The integral area determined in this way is fitted underneath the first derivative of each determination such that the first derivative of the polynomial is the boundary of the area at the top and, at the bottom, the intersection of the lower boundary straight lines with the curve on the X-axis indicates where the start and the end of the measurement time period are located (FIG. 5).

The polynomial is calculated from the pairs of reaction kinetics values using the least-squares principle. The system of normalized equations is solved using the Gaussian algorithm, a method which is known per se to the person skilled in the art for solving non-linear regressions. The matched polynomial is advantageously 3rd order, but higher order polynomials can also be used.

The following examples explain the invention:

COMPARATIVE EXAMPLE a) Peak Rate Method

The Behringwerke TurbiTime System is a good example of a kinetic evaluation method (DE 33 47 162). It has a measurement chamber in which the reaction in each case takes place in a single cell. The measurements of the optical density continue until the maximum rate of reaction $V_{Max}$, the result of the measurement, is reached, and are then terminated.

The reagents for the system are set such that they allow a rapid reaction and, in the ideal case, the measurement can be terminated after just a few seconds. The time when $V_{Max}$ is reached is also evaluated. This allows a decision to be made on the side of the Heidelberger curve that is involved, and an incorrectly excessively low result can be virtually precluded.

b) Fixed Time Method

The Behringwerke nephelometers (BN, BN100, BNII) measure the increase in turbidity as light scatter. The evaluation method is called "fixed time" on the basis of the fixed reaction times. The result of the measurement is the turbidity difference between an initial value and a final value. The nephelometers are fully automatic systems in which the samples incubate simultaneously in a large number of cells, in order to allow a high throughput. The cells are moved past the measurement optics at regular intervals by a rotor in order to record the measurements. Reaction kinetics are thus obtained with measurement points at relatively long intervals, for example 16 seconds in the case of the BN II.

EXAMPLE 1

The New $V_{MaxLin}$ Method with 2-stage Evaluation

The method has two stages (FIG. 3, Tab. 1):

1. Determination of the optimum length of the main run reaction window ($t_{Lin}$)

In a first run, the maximum rate of reaction $V_{MaxPre}$ is sought over the profile of the entire kinetics using a small initial run reaction window. The size of the window is defined specifically for the respective test such that it is still within the linear region of the reaction even with high antigen concentrations. The rate of reaction determined in this way is still relatively inaccurate.

It is used to define the ideal size of the main run reaction window ($t_{Lin}$) for this antigen concentration. In this context, ideal means that virtually the entire part of the reaction which has a linear profile is used to define the rate of reaction. The reference table for the assignment of the rate of reaction and size of the main run reaction window is likewise determined empirically on a test-specific basis. (FIG. 2, Tab. 1).

2. Determination of the maximum rate of reaction ($V_{MaxLin}$)

a) Identification of the Minimum

At the start of a kinetic process, it is possible for the turbidity to fall before the actual reaction starts. This would result in an incorrectly excessively low $V_{MaxPre}$ being determined for a long $t_{Lin}$ (for example 360 seconds). This prevents the minimum being identified.

A very short reaction window is used to define the starting time of the reaction. In the example in FIG. 3 and Table 1, this is a time period of 40 seconds. The reaction window starts from time zero and continues as long as the gradient is negative. As soon as it reaches the first positive value, the first measurement point of the reaction window is also the first value which can be considered for the calculation of $V_{MaxLin}$.

b) Search for $V_{MaxLin}$

The main run reaction window ($t_{Lin}$) determined in the initial run is used to look for the maximum rate of reaction over the entire profile. If ($t_{Lin}$) is greater than the actual reaction duration, the rate is averaged over the entire reaction (from the minimum to the end of the reaction time).

The rate of reaction $V_{MaxPre}$ determined in this way is used to produce the reference curves, and the reference curve is used to calculate the concentrations.

EXAMPLE 2

$V_{MaxLin}$ Method with Integral Evaluation for the Ferritin Test

The example uses the same pairs of measurements for Ferritin as Example 1.

a) Identification of the Minimum

The identification of the minimum is carried out as is described for Example 1 in 2a). For the low-concentration sample (Table 1), that is to say, a minimum is once again found at 38 seconds, and for the high-concentration sample at 0 seconds. All the measurement points before the minimum are now no longer considered.

b) Polynomial Matching

A third order polynomial is matched to the curve after the minimum, and its first derivative is formed (see also FIG. 5). The maximum of the first derivative occurs at 153 seconds for the low-concentration sample, and at 87 seconds for the high-concentration sample.

c) Finding the Evaluation Region $t_{Lin}$

An integral area underneath the maximum of the first derivative is enlarged iteratively until the limit, in this example 100, is reached (see also FIG. 5). At the same time, the area to the left and right of the time of the maximum of the first derivative is enlarged separately until the nominal area is reached. The reaction time window is obtained in this way. If the nominal area on the right-hand side does not extend to the last measurement point, the right-hand evaluation region extends to the last measurement point. If the nominal area on the left-hand side does not extend as far as the minimum, the reaction time window there extends to the minimum.

For the low concentration, the reaction time window is the same as for the $V_{MaxPre}$ method with 2 stages of evaluation from 38 to 360 seconds, and for the high concentration the reaction time window extends from 0 to 196 seconds.

d) Determination of the Raw Value

The raw value is obtained by linear regression within the reaction time window. This is 0.123 bits/second for the low concentration and 23.46 bits/second for the high concentration, in comparison with 23.64 bits/second in Example 1.

This value is either entered on a reference curve or is used with an existing reference curve to determine a concentration.

The elementary advantage of the $V_{MaxLin}$ method over the prior art is the ideal matching of the reaction window to the respective reaction kinetics by the two-stage method or the integral method, which uses empirically defined, test-specific parameters. If necessary, they could even be defined on a batch-specific basis.

Figure 6:
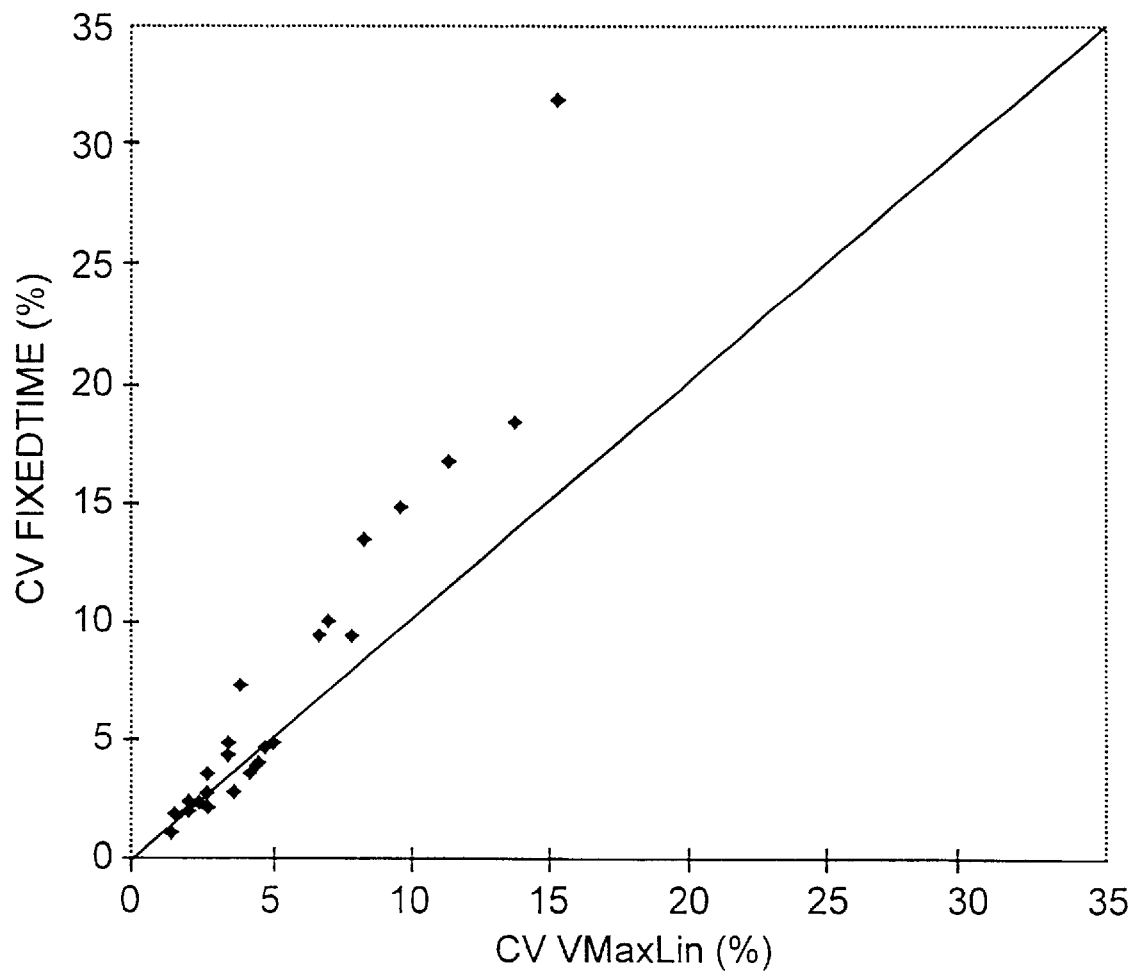
FIG. 6 shows a comparison of signal precision.

The very specific matching ensures that a maximum number of measurement points are used in each case for evaluation. This advantage is particularly evident when the signal-to-noise ratio is large, as is the case for the latex-enhanced tests on the BNII and, particularly in that case, with low analyte concentrations. The signal precision is better than that with the fixed time method, which uses only the difference between the initial and final values (FIG. 6).

The peak rate method is matched to kinetics, whose profiles have separations between a lag phase, the maximum rate of reaction and the saturation region (U.S. Pat. No. 4,157,871). In the case of the reaction profiles for the latex tests on the BNII (for example N Latex Ferritin), the lag phase and the saturation phase can often scarcely be identified (FIGS. 1a–1c). At the start of the reaction, the first measurement is taken too late and the frequency at which the measurements are taken is also too low for the lag phase still to be recorded. After 6 minutes, the saturation region is not reached by a long way.

If the three phases are not clearly separated and, in addition, the frequency at which the measurements are taken is relatively low, there is a risk that peak rate methods will incorrectly give excessively high maximum rates. Particularly withlow-concentration samples, such as that for example in FIGS. 1a–1c, there is clearly no point in determining a peak rate, since the rate of reaction is constant at a low level. This is also shown by the comparison of the accuracies with a short time window of 80 seconds, with which peak rates are still detected, and a reaction window of 360 seconds (FIG. 7).

A range of criteria have been used to assess the new evaluation method comparatively (Table 3). In all the experiments, the same kinetics were evaluated using the conventional fixed time method and the new method. In this case, the test time was shortened to 6 minutes from the previous 12 minutes for $V_{MaxLin}$, and the reference curve was extended. This resulted in a measurement range from 2.5 to 700 µg/l instead of 5–350 µg/l (initial sample dilution 1:5, FIG. 11).

Table 3

Ferritin—test characteristics in comparison with the fixed time and $V_{MaxLin}$ evaluation methods The LogitLog function was used for the reference curve for both methods. Each result represents the mean value of 10 measurements. Further descriptions can be found in the text.

TABLE 3

|  | Fixed Time | $V_{MaxLin}$ |
|---|---|---|
| Test time | 12 Minutes | 6 Minutes |
| Lower measurement range limit | 5 μg/l | 2.5 μg/l |
| Upper measurement range limit | 350 μg/l | 700 μg/l |
| Antigen excess certainty up to | 25000 μg/l | 50000 μg/l |
| Dilution trueness of samples Recovery 1:20 to 1:5 |  |  |
| 300–340 μg/l | +16.0% | +6.6% |
| 553–665 μg/l | —* | +6.7% |
| Intra Assay Precision Standard |  |  |
| 1:2.5 | 1.8% | 1.8% |
| 1:5 | 2.8% | 3.6% |
| 1:10 | 4.9% | 5.0% |
| 1:20 | 2.8% | 2.7% |
| 1:40 | 2.4% | 2.1% |
| 1:80 | 4.0% | 4.5% |
| 1:160 | 4.8% | 3.4% |
| 1:320 | 14.8% | 9.6% |
| 1:640 | 31.9% | 15.3% |
| Samples |  |  |
| Mean value (10) | 4.7% | 3.4% |
| Controls |  |  |
| High (153 μg/l) | 2.9% | 3.2% |
| Low (20.2 μg/l) | 6.1% | 4.6% |
| Inter Assay Precision Samples |  |  |
| Mean value (5) | 2.0% | 1.8% |
| Controls |  |  |
| High (153 μg/l) | 4.0% | 2.6% |
| Low (20.2 μg/l) | 4.6% | 2.9% |
| Control recovery |  |  |
| High (153 μg/l) | +2.2% | +3.6% |
| Low (20.2 μg/l) | +2.4% | +3.8% |

*outside the measurement range

Correlation (50 samples): $V_{MaxLin}$=0 951* Fixed Time—0.2785

The precision is equally good both in the series (intra assay) and between days (inter assay) for high and medium analyte concentrations. For low analyte concentrations, the precision for $V_{MaxPre}$ is considerably better than for the conventional method (Table 3).

Figure 9B:
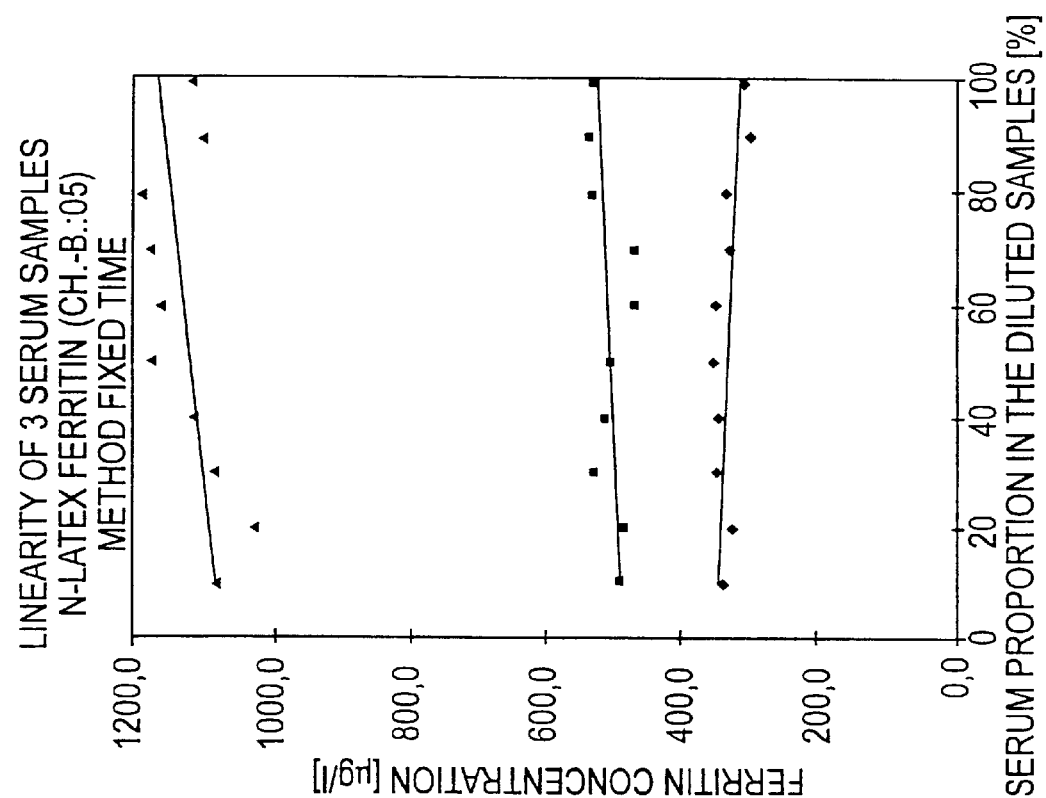
FIGS. 9a and 9b show the linearity of a dilution series.
Figure 9A:
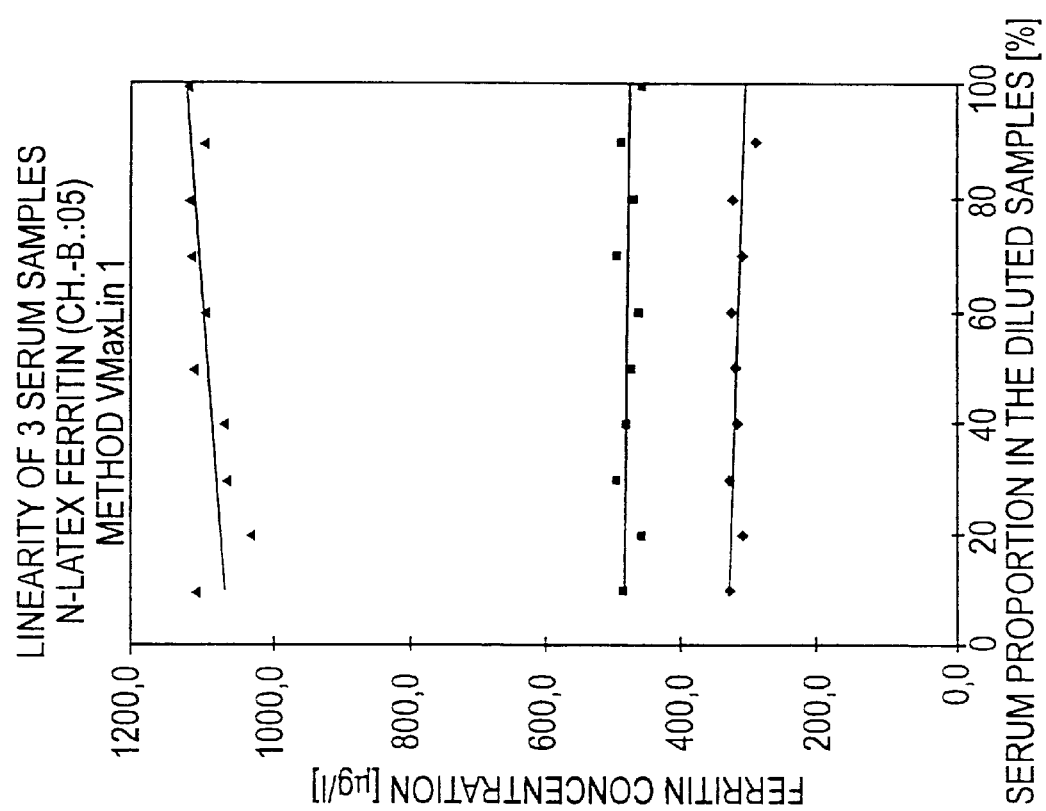

The dilution trueness is considerably better for $V_{MaxLin}$ (Tab. 3, FIG. 9). Particularly in the case of samples whose concentration is at the upper end of the measurement range, a repeat measurement at the next higher sample dilution (1:20) leads to values which are, on average, higher by 16%. The same experiment with the concentration twice as high for the extended measurement range leads to only 7% higher concentrations with $V_{MaxLin}$. FIG. 9 also shows the improved dilution trueness.

The control recovery is similarly good for both evaluation methods (Table 3). In this case, it must be remembered that the nominal value determination was carried out using the fixed time method, so that conversion here allows still better recovery to be expected.

Figure 10:
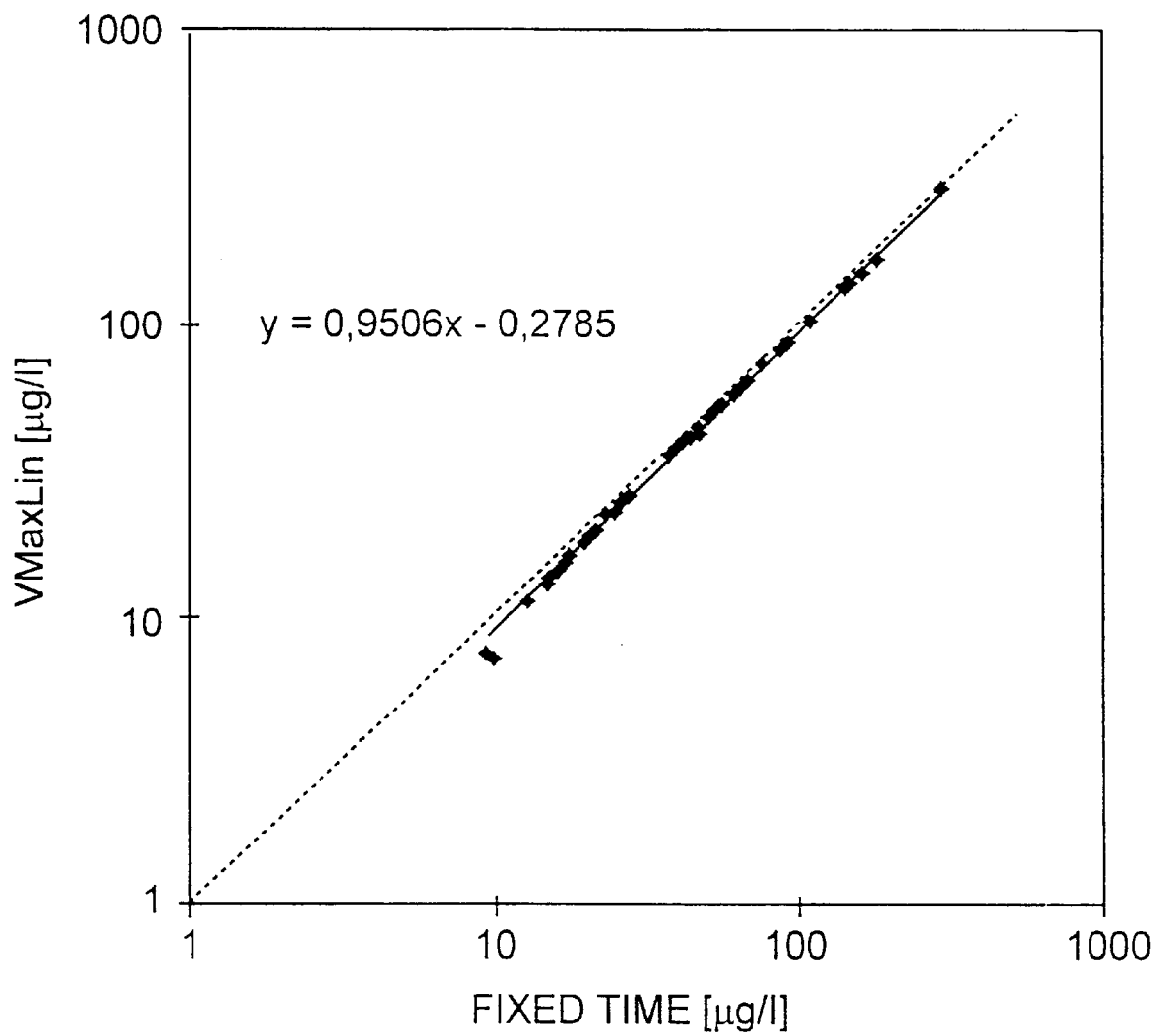
FIG. 10 shows a comparison of $V_{MaxLin}$ wit a fixed time evaluation for several samples.

The correlation of the results from both methods is very good (FIG. 10).

Figure 11:
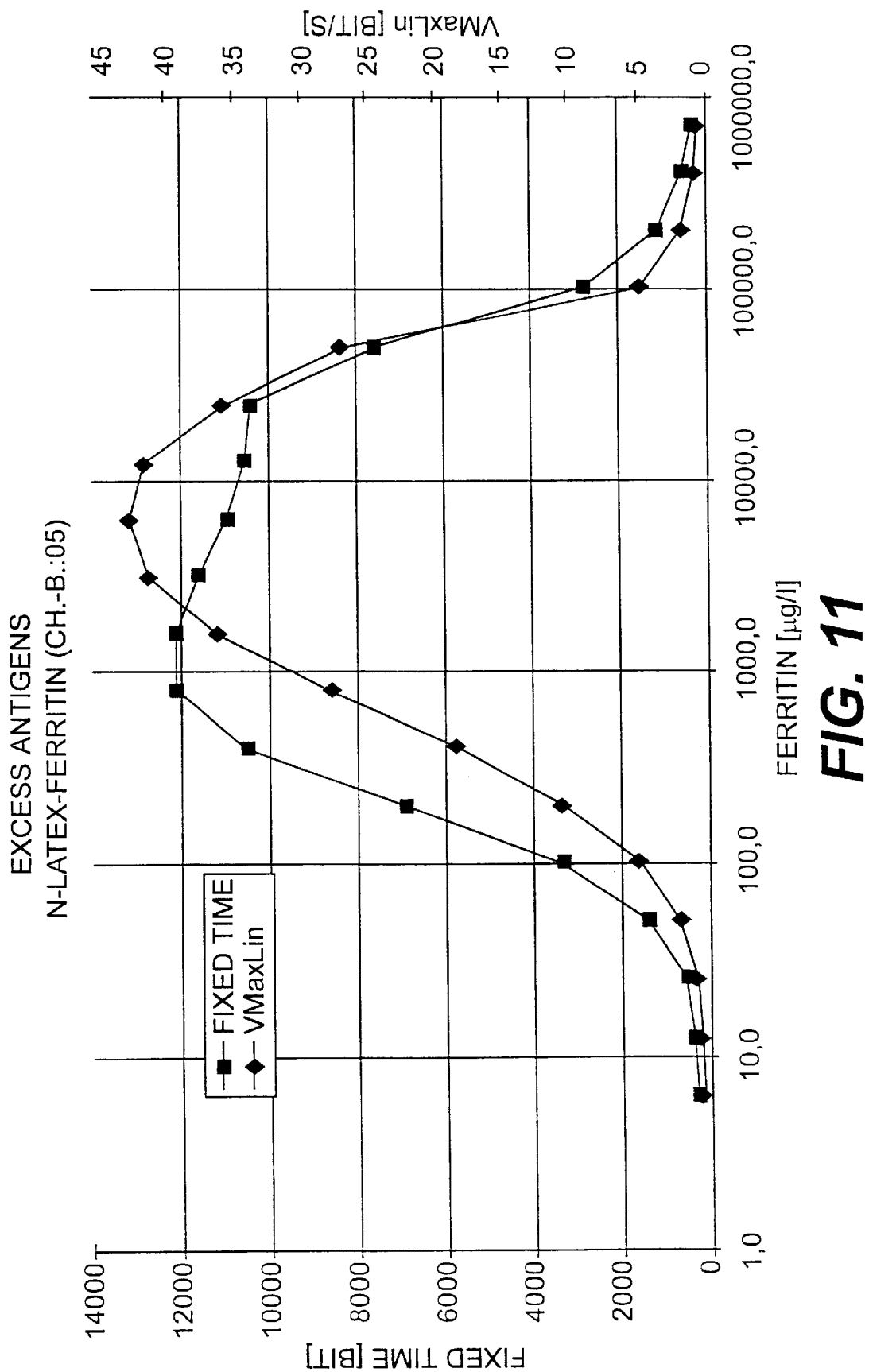
FIG. 11 shows antigen excess.

The antigen excess certainty is ensured up to about 25,000 g/l for fixed time and up to about 50,000 g/l for $V_{MaxPre}$ (FIG. 11).

Figure 8:
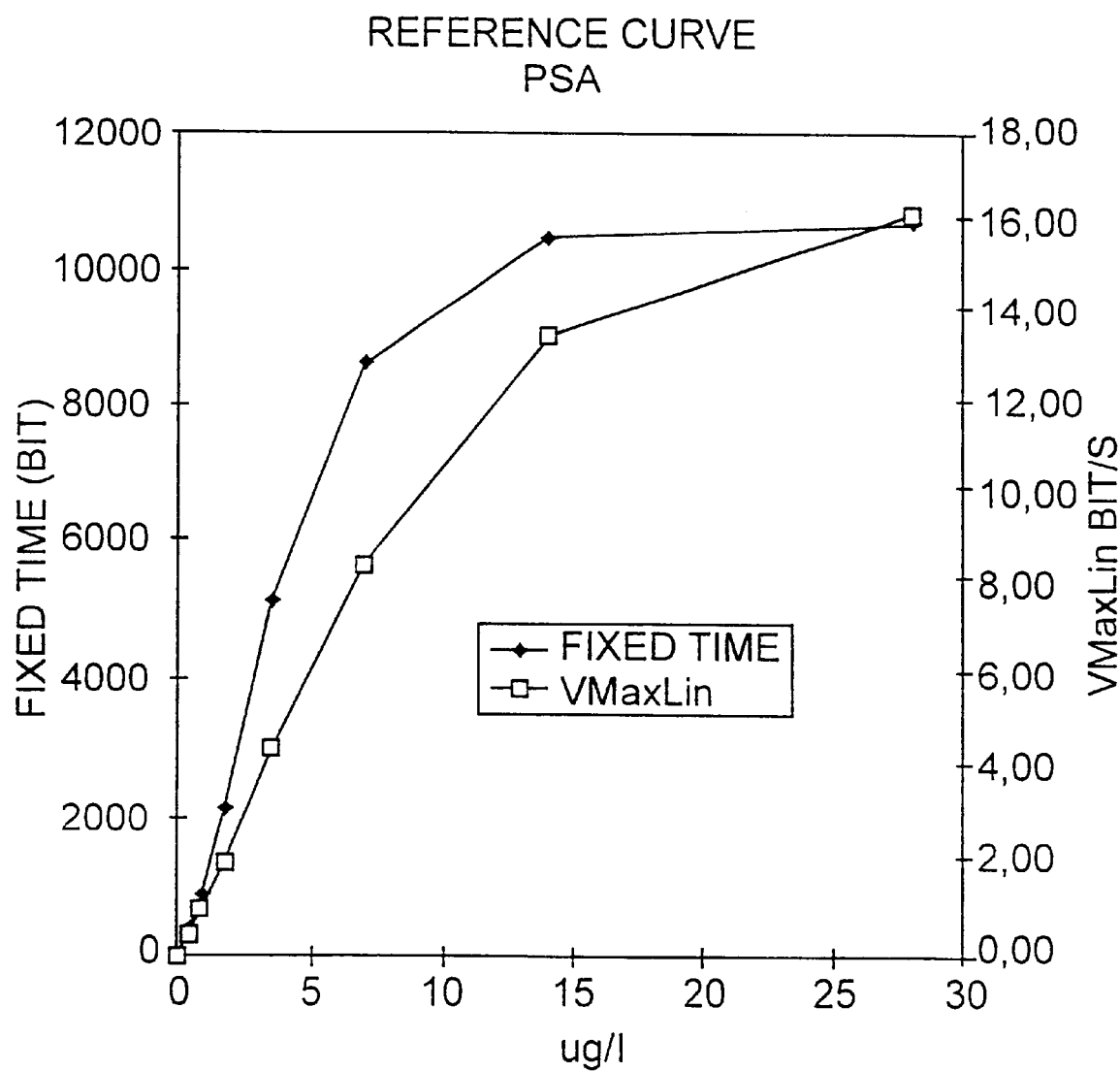
FIG. 8 shows a reference curve.

The test on PSA (prostate-specific antigen) can be used as a further example. As can be seen from FIG. 8, equally good reference curves can be produced using the $V_{MaxLin}$ method and promise that the measurement range can be extended upwards. In this case, the measurement time for $V_{MaxPre}$ is only 6 minutes, in comparison with 18 minutes for the fixed time method.

Table 4 compares the intra-assay precision (CV, %) from 10 measurements of the standard with fixed time, integral and two-stage evaluation for various latex-enhanced tests.

The two variants of the $V_{MaxLin}$ method are roughly equivalent and give considerably better accuracies than the fixed time method for low concentrations.

Table 4

A nominal area of 100 was used for the integral method
n.d.—value was not determined
*—mean value without zero standard Measurement Time:
  FRT 6 minutes(Integral and 2 stage)and 12 minutes (Fixed-time)
  PSA 12 minutes (Integral and 2 stage) and 18 minutes (Fixed-time)
  BR 9 minutes (Integral and 2 stage) and 12 minutes (Fixed-time)
  RF 6 minutes (Integral and 2 stage) and 6 minutes (Fixed-time)

| Dilution | Integral | | | | 2 stage | | | | Fixed-time | | | |
|---|---|---|---|---|---|---|---|---|---|---|---|---|
| 1: | FRT | PSA | BR | RF | FRT | PSA | BR | RF | FRT | PSA | BR | RF |
| 2.5 | 2.0 |  |  | 1.7 | 1.8 |  |  | 2.1 |  |  |  | 2.2 |
| 5 | 3.4 |  |  | 4.2 | 3.6 |  |  | 3.0 | 2.8 |  |  | 2.5 |
| 10 | 4.9 | 2.5 | 2.6 | 5.5 | 5.0 | 2.2 | n.d. | 4.1 | 4.9 |  | 2.4 | 3.7 |
| 20 | 3.0 | 4.5 | 2.9 | 3.1 | 2.7 | 5.4 | n.d. | 2.9 | 2.8 | 3.1 | 2.2 | 3.2 |
| 40 | 2.2 | 1.7 | 4.3 | 5.5 | 2.1 | 2.5 | n.d. | 5.0 | 2.4 | 1.1 | 4.1 | 5.3 |
| 80 | 4.8 | 2.7 | 6.3 | 6.4 | 4.5 | 2.8 | n.d. | 6.1 | 4.0 | 2.2 | 5.4 | 6.4 |
| 160 | 3.5 | 1.9 | 4.0 | 5.7 | 3.4 | 2.8 | n.d. | 4.2 | 4.8 | 1.8 | 4.9 | 8.5 |
| 320 | 9.7 | 2.3 | 8.2 |  | 9.6 | 3.8 | n.d. |  | 14.8 | 2.1 | 5.5 |  |
| 640 | 15.0 | 1.7 | 7.8 |  | 15.3 | 3.9 | n.d. |  |  | 2.0 | 13.6 |  |
| Zero standard |  | 16.9 |  |  |  | 17.9 |  |  |  | 32.1 |  |  |
| Mean value | 5.4 | 2.5 | 5.2 | 4.6 | 5.3 | 3.3 | n.d. | 3.9 | 5.2 | 2.1 | 5.4 | 4.5 |

EXAMPLE 3
(FIG. 12)

$V_{MaxLin}$ Method with Integral Evaluation for an aPTT Test

Figure 12A:
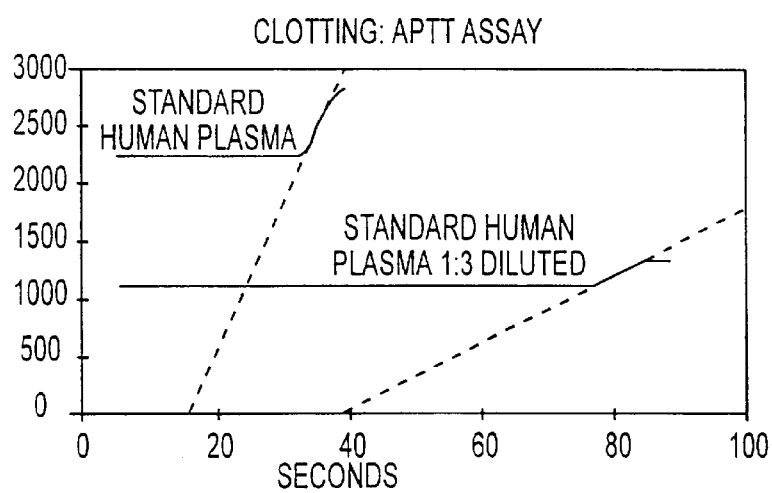
FIG. 12 shows the application of $V_{MaxLin}$ on different assay types.
Figure 12B:
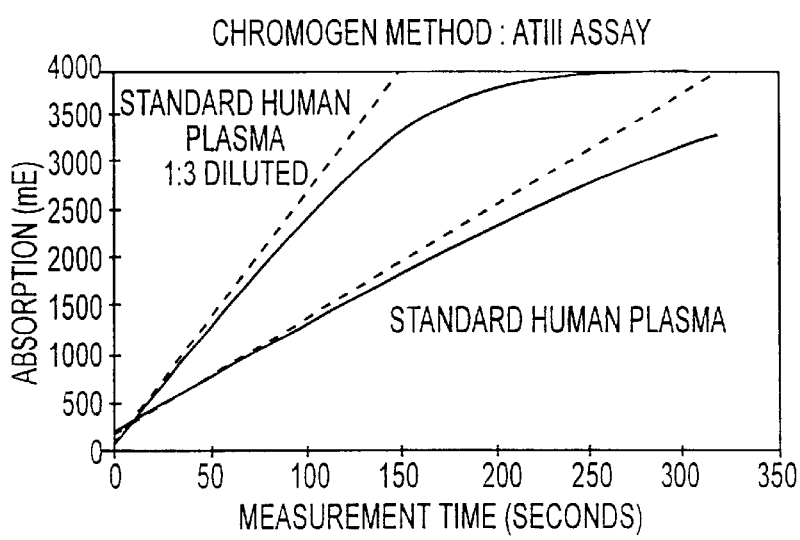
Figure 12C:
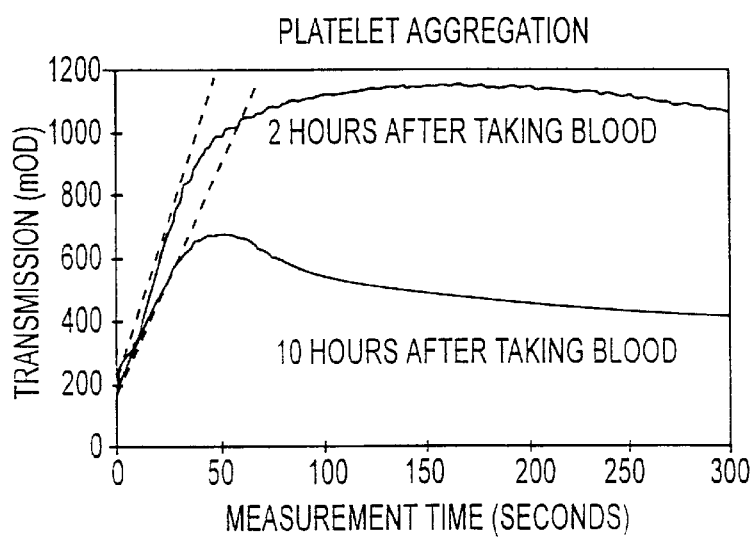

The evaluation is carried out for the Behring original test such that the time is determined at which a specific light absorption threshold is exceeded (fixed absorbance evaluation). It has been possible to show that the $V_{MaxPre}$ method with integral evaluation can be used just as well. The signal difference between the standard and the 1:3 diluted standard (125.7 mE/second compared with 28.2 mE/second) is higher than for the fixed absorbance evaluation (33.9 seconds compared with 81.4 seconds). It is advantageous that no threshold need be exceeded for the $V_{MaxPre}$ evaluation (system: BCS, Behring reagent OQGS, Behring test number: 28, nominal area: 10, polynomial order: 5, evaluation range: 30–100 seconds (undiluted standard), 70–150 seconds (1:3 standard), FIG. 12).

For $V_{MaxPre}$ evaluation of tests with a long lag phase, the starting time for the evaluation must be kept variable. This is done, for example, by an algorithm looking for a positive limit gradient in an analogous manner to the search for a minimum, the value of which gradient must be definable and depends on the test system. When the limit gradient is reached, the start of the search time window provides the starting time for the $V_{MaxLin}$ evaluation.

EXAMPLE 4
(FIG. 12)

$V_{MaxLin}$ Method with Integral Evaluation for an ATIII Test

The ATIII test, in which a chromogenic substrate is converted by the thrombin that is not inhibited by ATIII, can also be evaluated using $V_{MaxLin}$ (System: BCS, Behring reagent OWWR, Behring test number: 28, evaluation range: 0–45 seconds, nominal area: 1, polynomial order: 5). When measurements were carried out ten times, the accuracies were roughly just as good as those from conventional evaluation (slope from 15–45 seconds).

EXAMPLE 5
(FIG. 12)

$V_{MaxLin}$ Method with Integral Evaluation for a Platelet Aggregation Test

Widely different reaction kinetics may occur for the aggregation of blood platelets. The light transmission of the plasma increases in the course of aggregation. Using the example in FIG. 12, the profiles show the cell aggregation of a sample 2 hours and 10 hours after taking blood. In both profiles, $V_{MaxLin}$ with integral evaluation finds the linear section very well and determines an aggregation rate of 22.4 for the fresh sample and 14.5 for the old sample (System: BCT, Sample: 50 µl ADP (1.25 µM) from Sigma, St. Louis, USA, mixed with 150 µl of platelet-rich plasma, evaluation range: 7–80 seconds, nominal area: 5, polynomial order: 5).

EXAMPLE 6
(FIG. 13)

$V_{MaxLin}$ Method with Integral Evaluation for the Von-Willebrand Test

The Behring Von-Willebrand test determines the Von-Willebrand factor-dependent platelet aggregation using a reagent which contains fixed platelets and Ristocetin. The evaluation is carried out with the Behring original test such that the time is determined at which a specific threshold (100 mE) of the light absorption is undershot (fixed absorbance evaluation). The reference curve points may be determined only down to 20% Ristocetin co-factor concentration (standard human plasma dilution) using the conventional fixed absorbance evaluation since, below this, the threshold is no longer undershot because of the weak reaction, and thus it is no longer possible to determine any result at all. In contrast, $V_{MaxPre}$ with integral evaluation permits a reference curve down to about 5% for the same measurements (System: BCT, Behring reagent OUBD, Behring test number 390, evaluation range 7–80 seconds, nominal area: 5, polynomial order: 5).

What is claimed is:

1. A method for an instrument determination of the maximum rate value, $V_{Maxlin}$, of a measured variable, L(t), which changes with time, t, in a region with a linear profile using time and the period of a time window as variables within said region with said linear profile, comprising:

(a) measuring, in at least one preliminary experiment, said measured variable L(t);

(b) determining a relationship between the maximum rate value of said measured variable L(t) from said at least one preliminary experiment, $V_{MaxPre}$, and the period of the optimum time window, $t_{Lin}$;

(c) measuring, in at least one main run experiment, said measured variable L(t);

(d) determining the value of $V_{MaxPre}$ for said at least one main run experiment;

(e) determining the value of the period of the optimum time window $t_{Lin}$ by inputting the value of $V_{MaxPre}$ of step (d) into said relationship of step (b) for said at least one main run experiment; and (f) determining $V_{MaxLin}$, the maximum rate value of said L(t) measured in step (c) within said optimum time window of step (e).

2. A method according to claim 1, wherein, in steps (a) and (c), reacting a sample with at least one reagent leads to a time-dependent change of said measured variable L(t).

3. A method according to claim 2, wherein said sample comprises at least one analyte.

4. A method according to claim 3, wherein the concentration of said at least one analyte correlates to the maximum rate of said measured variable L(t).

5. A method according to claim 3, wherein said at least one analyte and said at least one reagent are partners in a specific bonding pair.

6. A method according to claim 5, wherein said at least one analyte and said at least one reagent are individually chosen from antigens and antibodies.

7. A method according to claim 3, wherein said at least one analyte is chosen from plasma proteins.

8. A method according to claim 3, wherein said at least one analyte is a haptene.

9. A method according to claim 1, wherein said L(t) is only partially linear.

10. A method according to claim 1, wherein determining said relationship in step (b) utilizes a previously determined, test-specific reaction time window $t_{Test}$.

11. A method according to claim 1, wherein determining the value of $V_{MaxPre}$ in step (d) utilizes a previously determined, test-specific reaction time window $t_{Test}$.

12. A method according to claim 1, further comprising performing a mathematical fit to said measured variable L(t).

13. A method according to claim 12, further comprising performing a first derivative of said mathematical fit.

14. A method according to claim 13, wherein determining said relationship in said step (b) utilizes said first derivative.

15. A method according to claim 13, wherein determining the value of $V_{MaxPre}$ in said step (d) utilizes said first derivative.

16. A method according to claim 12, wherein said mathematical fit is a polynomial fit.

17. A method according to claim 1, wherein said measured variable is the turbidity.

18. A method according to claim 1, wherein said measured variable is light scatter.

19. A method according to claim 1, wherein said method is for coagulation analysis.

20. A method for an instrument determination of the maximum rate value, $V_{MaxLin}$, of a measured variable, L(t), which changes with time, t, in a region with a linear profile using time and the period of a time window as variables within said region with said linear profile, comprising:

(a) measuring, in at least one separate run experiment, said measured variable L(t);

(b) determining the nominal area corresponding to the period of the optimum time window under the maximum value of the first derivative of said measured variable L(t);

(c) measuring, in at least one main run experiment, said measured variable L(t);

(d) determining the time of the maximum value of the first derivative of said measured variable L(t) of said at least one main run experiment;

(e) determining the value of the period of the optimum time window $t_{Lin}$ by expanding the nominal area under the maximum value of the first derivative of step (d) until the value of said nominal area of step (b) is reached to set the time period on both sides of the time of step (d); and (f) determining $V_{MaxLin}$, the maximum of said L(t) measured in step (c) within said optimum time window of step (e).

21. A method according to claim 20, wherein, in steps (a) and (c), reacting a sample with at least one reagent leads to a time-dependent change of said measured variable L(t).

22. A method according to claim 21, wherein said sample comprises at least one analyte.

23. A method according to claim 22, wherein the concentration of said at least one analyte correlates to the maximum rate of said measured variable L(t).

24. A method according to claim 22, wherein said at least one analyte and said at least one reagent are partners in a specific bonding pair.

25. A method according to claim 24, wherein said at least one analyte and said at least one reagent are individually chosen from antigens and antibodies.

26. A method according to claim 22, wherein said at least one analyte is chosen from plasma proteins.

27. A method according to claim 22, wherein said at least one analyte is a haptene.

28. A method according to claim 20, wherein said L(t) is only partially linear.

29. A method according to claim 20, further comprising performing a mathematical fit to said measured variable L(t).

30. A method according to claim 29, further comprising performing a first derivative of said mathematical fit.

31. A method according to claim 29, wherein said mathematical fit is a polynomial fit.

32. A method according to claim 20, wherein said measured variable is the turbidity.

33. A method according to claim 20, wherein said measured variable is light scatter.

34. A method according to claim 20, wherein said method is for coagulation analysis.

35. A method according to claim 20, further comprising performing a mathematical fit to said measured variable L(t).

36. A method according to claim 35, further comprising performing a first derivative of said mathematical fit.

37. A method according to claim 37, wherein determining said nominal area in said step (b) utilizes said first derivative.

38. A method for an instrument determination of the maximum rate value, $V_{MaxLin}$, of a measured variable, L(t), which changes with time, t, in a region with a linear profile using time and the period of a time window as variables within said region with said linear profile, comprising:

(a) measuring, in at least one separate run experiment, said measured variable L(t);

(b) measuring, in at least one main run experiment, said measured variable L(t);

(c) at least one step for determining the period of the optimum time window $t_{Lin}$; and (d) determining $V_{MaxLin}$, the maximum of said L(t) measured in step (b) within said optimum time window of step (c).

* * * * *

UNITED STATES PATENT AND TRADEMARK OFFICE
CERTIFICATE OF CORRECTION

PATENT NO.    : 6,317,702 B1
DATED         : November 13, 2001
INVENTOR(S)   : Jürgen Patzke It is certified that error appears in the above-identified patent and that said Letters Patent is hereby corrected as shown below:

Column 12,
Line 18, "$V_{Maxlin}$" should read -- $V_{MaxLin}$ --.

Column 14,
Line 30, "claim 37" should read -- claim 36 --.

Signed and Sealed this

Third Day of September, 2002

*Attest:*

*Attesting Officer*

JAMES E. ROGAN
*Director of the United States Patent and Trademark Office*